United States Patent [19]

Broom

[11] Patent Number: 4,517,124
[45] Date of Patent: May 14, 1985

[54] PROCESS FOR PREPARING PENEM DERIVATIVES

[75] Inventor: Nigel J. P. Broom, Reigate, England

[73] Assignee: Beecham Group Limited, England

[21] Appl. No.: 550,968

[22] Filed: Nov. 14, 1983

Related U.S. Application Data

[63] Continuation of Ser. No. 291,389, Aug. 10, 1981, abandoned.

[30] Foreign Application Priority Data

Aug. 16, 1980 [GB] United Kingdom ............... 8026733
Apr. 15, 1981 [EP] European Pat. Off. .......... 81301683

[51] Int. Cl.$^3$ ................ C07D 499/00; A61K 31/425
[52] U.S. Cl. ...................... 260/245.2 R; 260/245.2 T
[58] Field of Search ............... 260/245.2 R, 245.2 T; 424/270, 271

[56]  References Cited

U.S. PATENT DOCUMENTS 4,347,183  8/1982  Afonso et al. ............... 424/270
4,372,965  2/1983  Christensen et al. ......... 424/270
4,474,793 10/1984  Ross et al. ................... 424/270

Primary Examiner—Nicholas S. Rizzo
Attorney, Agent, or Firm—Jacobs & Jacobs

[57] ABSTRACT

The present invention provides a process for the preparation of a compound of the formula (IV):

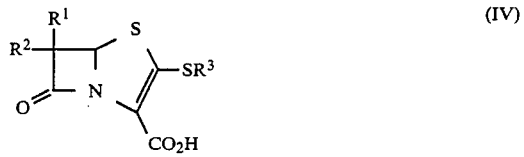

or salt or ester thereof wherein $R^1$ and $R^2$ are independently hydrogen; an organic radical bonded via a carbon atom to the ring carbon atom; a free, etherified or esterified hydroxy or mercapto group; an amino or acylamino group; or together $R^1$ and $R^2$ represent a group $=CR^5R^6$ wherein $R^5$ and $R^6$ are the same or different and each represent hydrogen or a hydrocarbon or heterocyclic group optionally substituted with a functional group; and $R^3$ represents an organic radical; which process comprises reacting a compound of the formula (V):

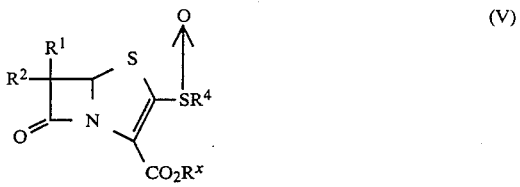

wherein $R^x$ is hydrogen or a blocking group and $R^4$ is an organic radical; with a thiol or reactive derivative thereof. The compounds of the formula (IV) are useful as antibiotics and β-lactamase inhibitors, as are the compounds of the formula (V). This invention also provides the novel compounds of the formula (V) and certain novel compounds within formula (IV). Their preparation and use are described.

7 Claims, No Drawings

PROCESS FOR PREPARING PENEM DERIVATIVES

This is a continuation of Ser. No. 291,389, filed Aug. 10, 1981, now abandoned.

This invention relates to a chemical process for preparing penem derivatives and in particular 2-substituted thio penem derivatives, which are useful in the treatment of antibacterial infections, either alone or in combination with other antibiotics.

Certain penem derivatives having a substituted thio group at the 2-position are known from European Patent Specification Nos. 2210 (Merck) and 13,662 (Schering) British Patent Specification No. 2,013,674 (Ciba-Geigy) and European patent application No. 813016839 (Beecham). These compounds have antibacterial and/or β-lactamase inhibitory properties. The structures of the compounds concerned can be represented by the formula (I) and salts and esters thereof:

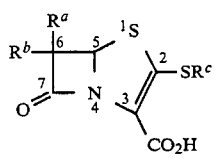

wherein $R^a$, $R^b$ and $R^c$ are various organic groups. The process by which compounds of formula (I) are readily accessible involves the cyclisation of an intermediate such as an ester of formula (II):

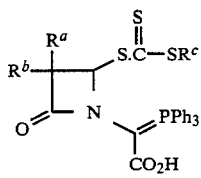

Compounds of formula (II) are derived from azetidinone compounds by reaction with a trithiocarbonate intermediate of formula (III) or a salt thereof:

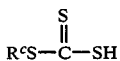

However compounds of formula (III) are only readily available when the group $R^c$ represents alkyl.

We have now found that penem derivatives of formula (I) can be prepared from derivatives having different group —$SR^c$. This process therefore enables the preparation compounds of formula (I) with hitherto less accessible substituents $SR^c$.

Our earlier British Patent Specification No. 2,036,015 does disclose a process for the introduction of a substituted thio group into the 2-position of a unsubstitued penem, but involves the use of a highly reactive compound such as a halo thio compound. The process of the present invention may be carried out using a thiol compound itself under mild conditions.

Accordingly the present invention provides a process for the preparation of a 2-thio penem derivative of formula (IV) or a pharmaceutically acceptable salt or in vivo hydrolysable ester thereof:

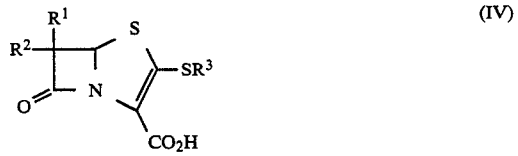

wherein $R^1$ and $R^2$ are independently hydrogen; an organic radical bonded via a carbon atom to the ring carbon atom; an free, etherified or esterified hydroxy or mercapto group; an amino or acylamino group; or together $R^1$ and $R^2$ represent a group $=CR^5R^6$ wherein $R^5$ and $R^6$ are the same or different and each represent hydrogen or a hydrocarbon or heterocyclic group optionally substituted with a functional group; and $R^3$ represents an organic radical; which process comprises reacting a sulphoxide of formula (V):

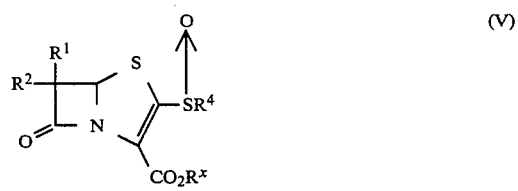

wherein $R^1$ and $R^2$ are as defined with respect to formula (IV) above, $R^x$ represents hydrogen or a carboxyl-blocking group and $R^4$ represents an organic radical different to the group $R^3$; with a thiol of formula (VI) or a reactive derivative thereof:

and thereafter if necessary carrying out one or more of the following steps:

(i) removal of any carboxyl-blocking group $R^x$;

(ii) converting the product to a pharmaceutically acceptable salt or in vivo hydrolysable ester group.

Pharmaceutically acceptable in vivo hydrolysable esters are those esters which hydrolyse in the human body to produce the parent acid or its salt. Such esters may be identified by administration to a test animal such as a rat or a mouse by intravenous administration and thereafter examining the test animal's body fluids for the presence of the compound of the formula (IV) or its salt.

Suitable ester groups of this type include those of part formulae (a), (b) and (c):

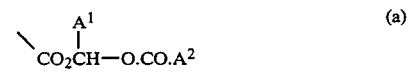

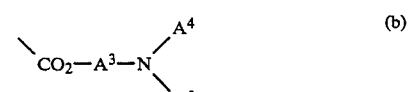

wherein $A^1$ is hydrogen, methyl, or phenyl, $A^2$ is $C_{1-6}$ alkyl, $C_{1-6}$ alkoxy or phenyl; or $A^1$ and $A^2$ together form a 1,2-phenylene group optionally substituted by one or two methoxy groups; $A^3$ represents $C_{1-6}$ alkylene optionally substituted with a methyl or ethyl group; $A^4$ and $A^5$ independently represent $C_{1-6}$ alkyl; $A^6$ represents $C_{1-6}$ alkyl. Examples of suitable in vivo hydrolysable ester groups include acetoxymethyl, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, diethylaminoethyl, phthalidyl and dimethoxyphthalidyl groups.

Suitable pharmaceutically acceptable salts of the 3-carboxylic acid group of the compound of formula (IV) include metal salts, eg aluminium, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabietylethylenediamine, or bases of the pyridine type such as pyridine, collidine or quinoline, or other amines which have been used to form salts with known penicillins.

When the thiol compounds of formula (VI) itself is employed, the reaction is generally carried out in the presence of a base, although this is not essential. Examples of suitable bases include sodium hydride, potassium hydride, sodium amide, potassium amide, sodium hydroxide, potassium hydroxide, sodium ethoxide, sodium methoxide, potassium butoxide, triethylamine, and tripropylamine. Advantageously, the base is used in an amount of at least 0.9 equivalent, preferably 1.0 to 1.2 equivalents, per mole of the thiol compound.

Instead of using the base in the reaction, a reactive derivative of the thiol compound of formula (VI) may be used. Preferably the reactive derivative is a salt of the thiol (VI), in particular a salt with an alkali metal, preferably sodium or potassium.

The amount of the thiol compound of formula (VI) or its reactive derivative is not critical. Generally, however, it is used in an amount of at least 1.0 mole, preferably 1.1 to 1.5 moles, per mole of the compound of formula (V).

The process of this invention may be carried out in any inert solvent such as N,N-dimethylformamide (DMF), tetrahydrofuran (THF), dioxane, hexamethyl phosphoramide (HMPA) or glyme. The solvent DMF is preferred. A low temperature is preferred, suitably below 0° C., preferably below −20° C. especially from about −30° C. to about −70° C.

Alternatively, when a salt of compound (VI) is employed, the reaction may be carried out in a two-phase reaction medium in the presence of a phase transfer catalyst. Examples of phase transfer catalysts are quaternary ammonium salts, tertiary amines, and crown ethers.

When the phase transfer catalyst is a quaternary ammonium salt, then suitable catalysts include those of formula

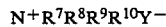

wherein $Y^-$ is an anion, $R^7$ and $R^8$ are $C_{1-18}$ organic groups, $R^9$ is a $C_{1-10}$ alkyl group, $R^{10}$ is a $C_{1-6}$ alkyl group, $R^8$, $R^9$ and $R^{10}$ and the nitrogen to which they are attached can form pyridine, and $R^7, R^8, R^9, R^{10}N^+$ contains at least nine carbon atoms.

The anion Y will normally be a halide such as a chloride or bromide, preferably a bromide, as quaternary ammonium salts are conventionally prepared by heating a tertiary amine with an organic halide.

Suitable quaternary ammonium salts are those derived from the cations: tertrabutylammonium, tetrapropylammonium, tributylethylammonium, cetylpyridinium, trioctylmethylammonium, cetyltriethylammonium, and benzyldimethyl-n-hexadecyl ammonium.

The phase transfer catalyst may also be a tertiary amine, in which case suitable catalysts include amines of the formula $R^{11}R^{12}R^{13}N$ wherein the R groups are each $C_{1-12}$ alkyl groups and the amine must contain at least 7 carbon atoms. Preferably at least $R^{11}$ and $R^{12}$ are $C_{3-10}$ straight chain alkyl groups.

A particularly useful tertiary amine phase transfer catalyst is dioctylmethylamine.

Crown ethers have also been found to be useful phase transfer catalysts. Examples of suitable crown ethers include dibenzo-18-crown-6, and dicyclohexyl-18-crown-6.

Suitable water-immiscible organic solvents include chlorinated hydrocarbon solvents such as methylene dichloride and chloroform; common ester solvents such as ethyl acetate and isopropyl acetate; and methyl isobutyl ketone.

The phase transfer reaction is conveniently carried out at a temperature of 0°–25° C., preferably 0°–5° C.

Suitable carboxyl-blocking derivatives for the group —$CO_2R^x$ in formula (V) include salts, esters, and anhydride derivatives of the carboxylic acid. The derivative is one which may readily be cleaved at a later stage of the reaction. The salts need not be pharmaceutically acceptable. Suitable salts include inorganic salts, for example metal salts such as silver or mercuric salt, or alkali metal salts such as the lithium or sodium salt, tertiary amine salts, such as those with tri-lower-alkylamines, N-ethylpiperidine, dimethylpiperazine. A preferred salt is with triethylamine.

Suitable ester-forming carboxyl-blocking groups are those which may be removed under conventional conditions. Such groups for $R^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, an oxime radical of formula —N=CHR° where R° is aryl or heterocyclic, or an in vivo hydrolysable ester radical as defined above.

The carboxyl group may be regenerated from any of the above esters by usual methods appropriate to the particular $R^x$ group, for example, acid- and base-catalysed hydrolysis, or by enzymically-catalysed hydrolysis, or by hydrogenation. The hydrolysis must of course be carried out under conditions to which the groups on the rest of the molecule are stable.

When it is desired to produce a compound of formula (II) in the form of a free acid or salt by the process of this invention, a compound of formula (V) is generally employed wherein $R^x$ is a carboxyl-blocking group. For the preparation of a compound of formula (IV) in the form of a pharmaceutically acceptable ester, it is convenient to employ a compound of formula (V) wherein $R^x$ represents the desired ester group.

The group $R^3$ may be a saturated or unsaturated, optionally substituted aliphatic, cycloaliphatic, cycloaliphatic-aliphatic, aromatic or araliphatic hydrocarbon radical having up to 18, preferably up to 10, carbon atoms, or an optionally substituted heterocyclyl or heterocyclyl-alkyl radical having up to 10 carbon atoms and up to 4 ring hetero atoms selected from the group nitrogen, oxygen and/or sulphur.

Suitably optional substituents on the group $R^3$ include amino, mono-, di- and tri-$(C_{1-6})$alkylamino, $C_{1-6}$alkanoylamino, hydroxyl, $C_{1-6}$alkoxyl, mercapto, $C_{1-6}$alkylthio, arylthio such as phenylthio, sulfamoyl, amidino, guanidino, nitro, chloro, bromo, fluoro, cyano, carboxyl, $C_{1-6}$alkoxycarbonyl, and $C_{1-6}$alkanoyloxy.

Suitably $R^3$ is one of the following groups optionally substituted with one or more of the above listed substituents: $C_{1-6}$alkyl, $C_{2-6}$alkenyl, aryl such as phenyl, aralkyl wherein the aryl moiety is preferably phenyl and the alkyl has 1-6 carbon atoms such as benzyl, phenethyl; heterocyclyl or heterocyclylalkyl wherein the alkyl has 1-3 carbon atoms and the heterocyclic ring comprises 4-6 atoms, up to 4 of which may be selected from oxygen, sulphur and nitrogen; such as pyridyl, pyrimidyl, furyl and thienyl.

Examples of the group $R^3$ include methyl, ethyl, phenyl, pyridyl, ethoxycarbonylvinyl, acetamidovinyl, pyrimidyl, aminophenyl, aminomethyl, aminoethyl, hydroxymethyl, hydroxyethyl, carboxymethyl, carboxyethyl, 2-amino-2-ethoxycarbonylethyl, acetamidomethyl, and acetamidoethyl.

Preferably the group $R^3$ is one which is not readily accessible by other methods, for example $C_{2-6}$ alkenyl such as vinyl, aryl such as phenyl, and heterocyclyl such as pyridyl or pyrimidyl.

Preferably one of the groups $R^1$ or $R^2$ is hydrogen.

When the group $R^1$ or $R^2$ represents an organic radical, it may be substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the linear chain has 1-6 carbon atoms; heteroaryl, heteroaralkyl, heterocyclyl and heterocyclylalkyl wherein the substituent or substituents relative to the above-named radicals are selected from the group consisting of: amino, mono-, di- and tri-alkylamino, hydroxyl, alkoxyl, alkanoyloxy mercapto, alkylthio, arylthio such as phenylthio, sulfamoyl, amidino, guanidino, nitro, chloro, bromo, fluoro, cyano and carboxy, and wherein the hetero atom or atoms in the above-named heterocyclic moieties are selected from the group consisting of 1-4 oxygen, nitrogen or sulphur atoms; and wherein the alkyl moieties of the above-recited substituents have 1-6 carbon atoms.

Preferably one of $R^1$ and $R^2$ is hydrogen and the other is hydroxyalkyl containing up to 6 carbon atoms, in particular α-hydroxyethyl, or acyloxy$(C_{1-6})$alkyl, such as α-acetoxyethyl.

When a group $R^1$ and $R^2$ is acylamino, suitable acylamino groups include groups of formulae (d), (e), (f) or (g):

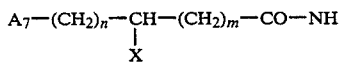 (d)

$A_8$—CO—NH (e)

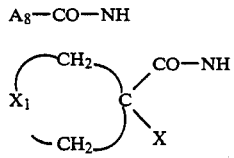 (f)

$A_8$—$X_2$—$(CH_2)_n$—CO—NH (g)

wherein n is 0, 1 or 2; m is 0, 1 or 2; $A_7$ is an alkyl group of 1-6 carbon atoms, a cycloalkyl group of 3-6 carbon atoms, cyclohexenyl, cyclohexadienyl, phenyl hydroxyphenyl, thienyl or pyridyl group; X is a hydrogen, bromine or chlorine atom, a carboxylic acid, carboxylate ester, hydroxy, acyloxy, amino, ureido, guanidino or acylureido group; $A_8$ is an aromatic group such as a phenyl, 2,5-dimethoxyphenyl, 2-alkoxy-1-naphthyl, 3-arylisoxazolyl, isothiazolyl or 3-aryl-5-methylisoxazolyl group; $X_1$ is a $CH_2OCH_2$, $CH_2SCH_2$ or $(CH_2)_n$ group; and $X_2$ is an oxygen or sulphur atom. For example, phenylacetamido, p-hydroxyphenylacetamido, o-hydroxyphenylacetamido, m-hydroxyphenylacetamido, α-chlorophenylacetamido, α-bromophenylacetamido, α-carboxyphenylacetamido and esters thereof such as the tolyl, indanyl and phenyl esters, α-azidophenylacetamido, α-aminophenylacetamido, α-hydroxyphenylacetamido, α-ureidophenylacetamido, α-guanidinophenylacetamido, α-(acetylureido)-phenylacetamido, α-acetoxyphenylacetamido, α-tetrazolylphenylacetamido, acetamido, chloroacetamido, bromoacetamido, propionamido, pyridylacetamido, 2-thienylacetamido, 3-thienylacetamido, 2-thienylpropionamido, 3-thienylpropionamido, α-chloro(p-hydroxyphenyl)acetamido, α-bromo(p-hydroxyphenyl)acetamido, α-carboxy(p-hydroxyphenyl)acetamido and esters thereof such as the tolyl, indanyl and phenyl esters, α-amino(p-hydroxyphenyl)acetamido, α-hydroxy(p-hydroxyphenyl)acetamido, α-acetoxy(p-hydroxyphenyl)acetamido, α-ureido(p-hydroxyphenyl)acetamido, α-guanidino(p-hydroxyphenyl)acetamido, α-acetylureido(p-hydroxyphenyl)acetamido, phenoxyacetamido, o-hydroxyphenoxyacetamido, m-hydroxyphenoxyacetamido, p-hydroxyphenoxyacetamido, methoxyacetamido, ethoxyacetamido, α-amino(p-hydroxy)phenoxyacetamido, α-aminophenoxyacetamido, α-acetylphenoxyacetamido, α-acetyl(p-hydroxy)phenylacetamido, α-hydroxyphenoxyacetamido, α-hydroxy(p-hydroxy)-phenylacetamido, α-carboxyphenoxyacetamido and esters thereof such as the tolyl, indanyl and phenyl esters, α-carboxy(p-hydroxy)phenoxyacetamido and esters thereof such as the tolyl, indanyl and phenyl esters, phenoxypropionamido, phenoxybutyramido, benzamido, 2,6-dimethoxybenzamido, 2-ethoxy-1-naphthamido, 2-methoxy-1-naphthamido, 2-propoxy-1-naphthamido, 3-phenyl-5-methyl-4-isoxazolylcarboxamido, 3-o-chlorophenyl-5-methyl-4-isoxazolylcarboxamido, 3-o,o-dichlorophenyl-5-methyl-4-isoxazolylcarboxamido, isothiazolylcarboxamido, 3-o,o-fluorochlorophenyl-5-methyl-4-isoxazolylcarboxamido, 3-phenyl-4-isoxazolylcarboxamido, 3-o-chlorophenyl-4-isoxazolylcarboxamido, 3-o,o-dichlorophenyl-4-isoxazolylcarboxamido, 3-o,o-fluorochlorophenyl-4-isoxazolylcarboxamido, 1-aminocyclohexyl-1-carboxamido, phenylthioacetamido, phenylthiopropionamido and p-hydroxyphenylthioacetamido.

When the groups $R^1$ and $R^2$ together represent a group $=CR^5, R^6$, suitably $R^5$ and $R^6$ are independently hydrogen or a $C_{1-10}$ hydrocarbon group, especially $C_{1-6}$ alkyl or phenyl. Preferably one of $R^5$ and $R^6$ is hydrogen. Preferably one of $R^5$ and $R^6$ is methyl, ethyl or phenyl.

Compounds of formula (V) are novel compounds and form part of this invention. The free acids and pharmaceutically acceptable salts of compounds (V) have utility as antibacterial agents and all the compounds of formula (V) are useful as intermediates. They may be prepared by S-oxidation of a compound of formula (VII):

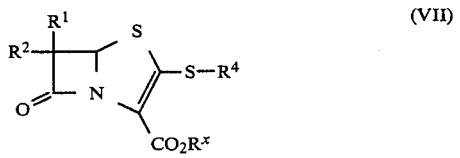
(VII)

wherein $R^1$, $R^2$, $R^4$ and $R^x$ are as defined with respect to formula (V) above; with a mild oxidising agent.

Suitable mild oxidising agents include perbenzoic acid, hydrogen peroxide, selenium dioxide or sodium metaperiodate. Substituted perbenzoic acids such as m-chloroperbenzoic acid are most preferred.

We have surprisingly found that oxidising agents selectively oxidise the exocyclic sulphur atom without affecting the ring sulphur atom at the 1-position in the penem ring.

The reaction between the compound of formula (VII) and the oxidizing agent is conveniently carried out in an inert solvent such as methylene chloride, chloroform or carbon tetrachloride at room temperature or at a lower temperature, preferably about $-30°$ C. to about $20°$ C.

The amount of the oxidizing agent used in the oxidation of the compound of formula (VI) can be varied widely depending upon the type of the oxidizing agent, the reaction conditions, etc. Generally, the advantageous amount of the oxidizing agent is 0.3 to 2 molar equivalents, preferably 1 to 1.7 molar equivalents, per mole of the compound of formula (VI).

After the reaction, the sulphoxide of formula (V) can be isolated and purified by various methods known per se. Usually this compound can be isolated from the reaction mixture by methods frequently utilized in the isolation and purification of carboxyl-containing antibiotics. Furthermore, the compound of formula (V) can be used in the aforesaid reaction without isolation and purification.

The compounds of formula (VII) may be prepared by the methods described in European Patent Specifications Nos. 2210 and 13,662, British Patent Specification No. 2,013,674, and European Patent Application No. 81301683.9.

Because the free acid form of compounds of formula (V) are useful as antibacterial agents, the present invention also provides a pharmaceutical composition which comprises a compound of the formula (V) wherein $R^x$ is hydrogen, or a pharmaceutically acceptable salt or in vivo hydrolysable ester thereof and a pharmaceutically acceptable carrier.

If the compound of the invention present in such a composition is in the form of a salt then suitable salts include pharmaceutically acceptable alkali metal or alkaline earth metal salts, or a salt with a pharmaceutically acceptable nitrogenous base. Particularly suitable salts include the sodium salt and the potassium salt.

The compositions may be formulated for administration by any route, for example oral, topical or parenteral, although an oral administration is preferred. The compositions may be in the form of tablets, capsules, powders, granules, lozenges, or liquid preparation, such as oral or sterile parenteral solutions or suspensions.

The invention also provides synergistic pharmaceutical compositions which comprise a pharmaceutical composition as hereinbefore described which also contains a penicillin or a cephalosporin.

Suitable penicillins for inclusion in the compositions of this invention include benzyl penicillin, phenoxymethylpenicillin, ampicillin, amoxycillin, carbenicillin, ticarcillin, suncillin, sulbenicillin, azlocillin, mezlocillin, apalcillin, piperacillin or pro-drugs of these compounds.

Particularly suitable cephalosporins for inclusion in the compositions of this invention include cephaloridine, cephalexin, cephradine, cefazolin and cephalothin.

Many of the compounds of formula (IV) above have not previously been prepared because of less readily available starting materials. Such novel compounds also form part of this invention, and are described in the examples hereinafter. In particular the present invention also provides compounds of formula (IV) wherein $R^3$ represents an optionally substituted aromatic hydrocarbon group having up to 18 carbon atoms, preferably up to 10 carbon atoms; or an optionally substituted heterocyclyl group having up to 10 carbon atoms and up to 4 ring heteroatoms selected from nitrogen, oxygen and/or sulphur.

Suitable optional substituents are those described for the group $R^3$ above.

The comments above concerning pharmaceutical compositions are also applicable to these novel compounds.

The following preparations and Examples illustrate this invention.

PREPARATION 1

(Z)-2-Carboethoxyvinylisothiuronium Chloride

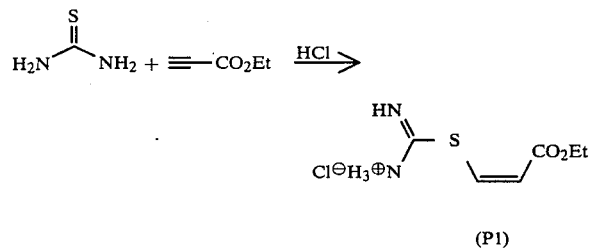

(P1)

A solution containing ethyl propiolate (9.8 g) in methanol (20 ml) was added to a solution of thiourea (7.6 g) in 2N hydrochloric acid at a rate which allowed the temperature of the exothermic reaction to be maintained at approximately 50° C. After the addition was complete the mixture was stirred for 2 hours and evaporated. The residue was re-evaporated from dry toluene (3×20 ml) and crystallised from propan-2-ol to give the isothiuronium chloride (P1) (14.2 g), mp 134°–136° C. (rods); $\nu$max (Nujol) 3600–2500, 1700, 1675, 1660 cm$^{-1}$; $\delta$ ppm [(CD$_3$)$_2$SO] 1.28 (3H, t, J 7 Hz), 3.69 br (1H, s, exch. D$_2$O), 4.26 (2H, q, J 7 Hz), 6.40 (1H, d, J 10 Hz), 7.96 (1H, d, J 10 Hz), 10.02 br (3H, s, exch. D$_2$O).

(Found: C, 34.1; H, 5.2; N, 13.3; S, 15.2. $C_6H_{11}N_2ClO_2S$ requires C, 34.2; H, 5.2; N, 13.3; S, 15.2%).

PREPARATION 2

(4RS)-3,3-Dibromo-1(1-methoxycarbonyl-2-methyl-prop-1-enyl)-4-methylthioazetidin-2-one

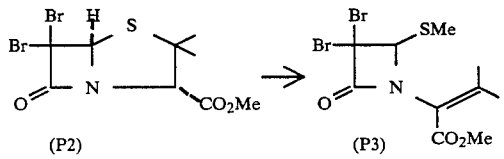

A mixture of methyl 6,6-dibromopenicillanate (J. P. Clayton, J. Chem. Soc. (C), 1969, 2123) (42.0 g), methyl iodide (42 ml) and finely powdered sodium hydroxide (5.4 g) in dry tetrahydrofuran (400 ml) was stirred at room temperature for 2.5 hours. The mixture was filtered and the filtrate concentrated. The resulting solution was diluted with ethyl acetate (1 liter) and washed with brine (3×100 ml). The dried ($MgSO_4$) organic layer was evaporated and the residue chromatographed on silica gel eluting with ethyl acetate/petroleum ether mixtures to give the secopenicillanate (23) (25.8 g) as an oil, $\nu_{max}$. ($CHCl_3$) 1785, 1725; δ ppm ($CDCl_3$) 2.00 (3H, s), 2.23 (3H, s) 2.32 (3H, s), 3.82 (3H, s), 5.52 (1H, s).

PREPARATION 3

(3ξ, 4RS)-3-Bromo-3[1-(ξ)-hydroxyethyl]-1(1-methoxycarbonyl-2-methylprop-1-enyl)-4-methylthioazetidin-2-one

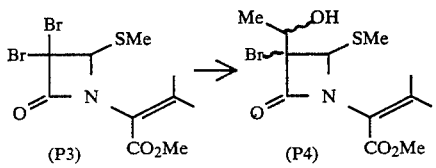

(a) Using methyl magnesium bromide

A solution of methyl magnesium bromide (2M in diethyl ether, 14.2 ml) was added, dropwise over five minutes, to a stirred solution of the dibromosecopenicillanate (P3) (10.0 g) indry tetrahydrofuran (200 ml) at −76° C. After stirring at −76° C. for a further twenty minutes a solution of acetaldehyde (3 ml) in dry tetrahydrofuran (10 ml) was added dropwise over five minutes. The mixture was stirred at −76° C. for a further ten minutes, treated with a saturated solution of ammonium chloride (10 ml), and allowed to attain room temperature. The mixture was diluted with ethyl acetate and the organic phase separated. The organic layer was washed with brine, dried ($MgSO_4$), and evaporated to give a crude gum. Chromatography of the crude product on silica gel eluting with ethyl acetate/petroleum ether mixtures gave the bromohydrin (P4) (7.28 g), a 9:1 mixture of isomers, as a viscous oil, $\nu_{max}$. ($CHCl_3$) 3600–3100, 1765, 1725 $cm^{-1}$; δ ($CDCl_3$) 1.43 (3H, d, J 6½ Hz), 2.04 (3H, s), 2.13 (3H, s), 2.28 (3H, s), 2.53 br (1H, d, J approx. 4 Hz, exch. $D_2O$), 3.78 (3H, s), 4.05–4.40 (1H, m, collapsing to 4.21, q, J 6½ Hz on exch. $D_2O$), 5.25 (0.9H, s), 5.32 (0.1H, s).

(b) Using n-butyl lithium

The above experiment was repeated using n-butyl lithium (one equivalent) in place of methyl magnesium bromide to give, after chromatography, the bromohydrin (P4) in 36% yield.

PREPARATION 4

(3RS,4RS) and (3RS,4SR)-3[1-(ξ)-Hydroxyethyl]-1(1-methoxycarbonyl-2-methylprop-1-enyl)-4-methylthioazetidin-2-one

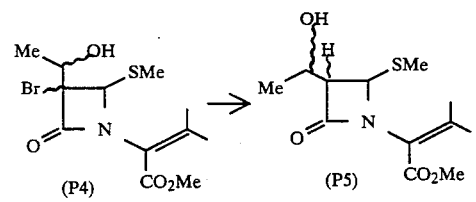

The bromohydrin (P4) (7.04 g) was stirred with zinc-silver couple (prepared from 2.60 g zinc dust according to the method of R. D. Clark and C. H. Heatcock, J. Org. Chem., 1973, 3659) in methanol (100 ml) containing glacial acetic acid (0.57 ml) at room temperature for ten minutes (the mixture was initially cooled with an ice-water bath in order to moderate a slightly exothermic reaction). The mixture was filtered through Kieselguhr, the residue being washed with a little methanol. The combined filtrates were evaporated to low volume and diluted with ethyl acetate. The solution was washed successively with N. hydrochloric acid, brine, dilute sodium bicarbonate solution, and brine. The dried ($MgSO_4$) organic layer was evaporated and the residual gum, chromatographed on silica gel eluting with ethyl acetate/petroleum ether mixtures to give a 3:1 mixture of the cis- and trans-hydroxyethylazetidinones (P5) (4.64 g) as a gum, $\nu_{max}$. ($CHCl_3$) 3600–3200, 1750, 1720 $cm^{-1}$; δ ppm ($CDCl_3$) 1.32 and 1.42 (3H, each d, J 6 Hz), 1.98 and 2.00 (3H, each s), 2.10, 2.17 and 2.24 (6H, each s), 2.35–2.90 (1H, broad signal, exch. $D_2O$), 3.14 (¼H, dd, J 2 and 5 Hz), 3.41 (¾H, dd, J 5 and 9 Hz), 7.75 (3H, s), 4.00–4.40 (1H, m, simplifies on exch. $D_2O$), 4.90 (½H, d, J 2 Hz), 5.04 (¾H, d, J 5 Hz).

PREPARATION 5

3-(1-Acetoxyethyl)-1-(1-methoxycarbonyl-2-methyl-prop-1-enyl)-4-methylthioazetidin-2-one

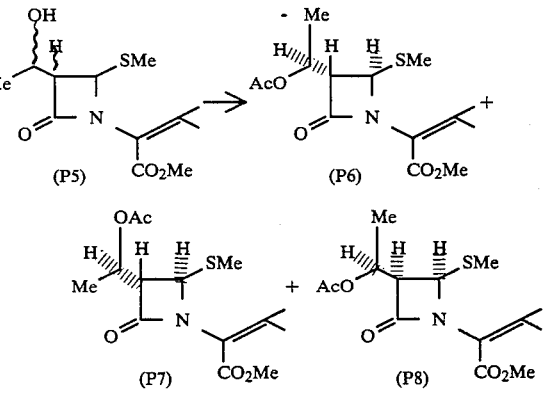

A solution of acetic anhydride (292 mg) in dry methylene chloride (2 ml) was added dropwise over 3 minutes to a stirred, ice-bath cooled, mixture of the hydroxyethylazetidinones (P5) (650 mg), triethylamine (288 mg) and 4-dimethylaminopyridine (26 mg) in dry methylene chloride (10 ml). After 45 minutes at ice-bath temperature the mixture was evaporated to low volume, diluted with ethyl acetate, and washed with dilute hydrochloric acid, brine, sodium bicarbonate solution, and brine. The dried (MgSO$_4$) organic layer was evaporated and chromatographed to give two fractions. The less polar fraction, the (3RS,4SR)-3-[1-(RS)-acetoxyethyl]azetidinone (P6), contaminated with approximately 25% of the (3RS,4SR)-3-[1-(SR)-acetoxyethyl]azetidinone (P7), was obtained as a gum (204 mg), $\nu$max (CHCl$_3$) 1760, 1730 sh. cm$^{-1}$; $\delta$ ppm (CDCl$_3$) 1.41 and 1.43 (3H, each d, J 7 Hz), 1.98–2.23 (12H, m), 3.18–3.37 (1H, m), 3.76 (3H, s), 4.91 (0.75 H, d, J 2 Hz), 4.99 (0.25 H, d, J 2 Hz), 5.15–5.50 (1H, m).

The more polar fraction, the (3RS,4RS)-3-[1-(SR)-acetoxyethyl]azetidinone (P8) (502 mg) was obtained as a waxy solid, m.p. 73°–5° C. (cubes ex ethyl acetate/petroleum ether), $\nu$max (CHCl$_3$) 1760, 1750 sh, 1730 sh. cm$^{-1}$; $\delta$ ppm (CDCl$_3$) 1.47 (3H, d, J 6.5 Hz), 1.99, 2.03 and 2.24 (12H, each s), 3.63 (1H, dd, J 5 and 9 Hz), 3.76 (3H, s), 5.07 (1H, d, J 5 Hz), 5.29 (1H, dq, J 6.5 and 9 Hz). (Found: C, 53.5; H 6.7; N, 4.4; S, 10.5; M$^+$, 315.1149. C$_{14}$H$_{21}$NO$_5$S requires C, 53.3; H, 6.7; N, 4.4; S, 10.2%; M, 315.1137).

PREPARATION 6

(3RS,4SR)-3-[1-(RS)-Acetoxyethyl]-4-methylsulphonylazetidin-2-one

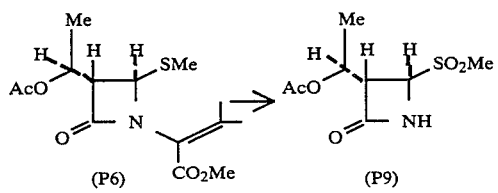

A solution of m-chloroperbenzoic acid (241 mg) in ethyl acetate (3 ml) was added dropwise over 2 minutes to a stirred, ice-bath cooled, solution of the impure azetidinone (P6) (200 mg) in ethyl acetate (10 ml). The stirred mixture was allowed to attain room temperature during 45 minutes and was washed with saturated sodium bicarbonate solution (2×5 ml) and brine (3×5 ml). The dried (MgSO$_4$) organic layer was diluted with ethyl acetate (15 ml), cooled to −20° and ozonised oxygen passed for 10 minutes. The excess ozone was removed by passage of argon and the mixture treated with methanol (15 ml). The mixture was kept at room temperature for 20 hours and evaporated to give a crude gum which was chromatographed on silica gel eluting with ethyl acetate/petroleum ether mixtures to give the sulphone (P9) (137 mg) contaminated with approximately 25% of the (3RS,4SR)-{1-(SR)-acetoxyethyl} isomer as a gum, $\nu_{max}$. (CHCl$_3$) 3550 br, 3410, 3300 br, 1795, 1745 cm$^{-1}$; $\delta$ ppm (CDCl$_3$) 1.41 and 1.43 (3H, each d, J 6.5 Hz), 2.03 and 2.08 (3H, each s) 2.95 (3H, s), 3.68 (dd, J 2 and 7 Hz) and 3.79 (dd, J 2 and 5 Hz) together 1H, 4.53 (¾H, d, J 2 Hz), 4.73 (¼H, d, J 2 Hz) 5.14–5.45 (1H, m), 7.05 (1H, br, signal).

PREPARATION 7

(3RS,4SR)-3-[1-(RS)-Acetoxyethyl]-4-ethylthiothiocarbonylthioazetidin-2-one

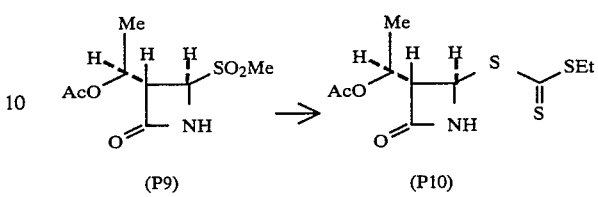

A solution of the impure sulphone (P9) (110 mg) in methylene chloride (5 ml) was cooled in an ice-bath and treated with a solution of potassium ethyltrithiocarbonate (91 mg) in water (1 ml). After 10 minutes at ice-bath temperature the stirred mixture was allowed to attain room temperature during 30 minutes. The organic phase was separated and the aqueous layer extracted with methylene chloride (2 ml). The combined organic layers were washed with brine (3×3 ml), dried (MgSO$_4$) and evaporated. Chromatography of the residue on silica gel eluting with ethyl acetate/petroleum ether mixtures gave the (3RS,4SR)-3-1-(RS)-acetoxyethyl azetidinone (P10) (97 mg) containing approximately 20% of the (3RS,4SR)-3-{1-(SR)-acetoxyethyl} isomer as impurity, $\nu_{max}$. (CHCl$_3$) 3610, 3410, 1780, 1740 cm$^{-1}$; $\delta$ ppm (CDCl$_3$) 1.35 (t, J 7 Hz), 1.37 (d, J 6 Hz) and 1.41 (d, J 6.5 Hz) together 6H, 2.03 and 2.07 (3H, each s), 3.2–3.5 (3H. m), 5.17–5.5 (1H, m), (5.43, 0.8H, d, J 2 Hz), 5.58 (0.2H, d, J 2 Hz), 6.5–6.8 br (1H).

PREPARATION 8

(3RS,4SR)-3-[1-(RS)-Acetoxyethyl]-4-ethylthiothiocarbonylthio-1-(1-hydroxy-1-p-nitrobenzyloxycarbonylmethyl)azetidin-2-one

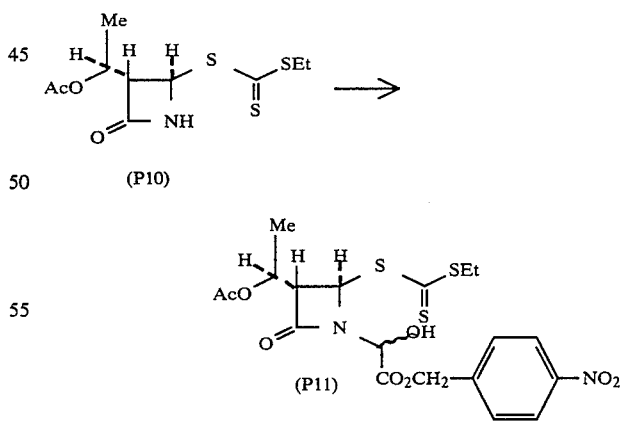

The impure azetidinone (P10) (1.0 g) and p-nitrobenzyl glyoxylate monohydrate (1.55 g) were heated in refluxing benzene (40 ml) under argon with provision for removal of water for 22 hours. The mixture was evaporated and chromatographed to give the hydroxyester (P11) (1.51 g), a mixture of stereoisomers, as a gum, $\nu_{max}$. (CHCl$_3$) 3600–3100, 1780, 1745 cm$^{-1}$.

PREPARATION 9

(3RS,4SR)-3-[1-(RS)-Acetoxyethyl]-1-(1-chloro-1-p-nitrobenzyloxycaarbonylmethyl)-4-ethylthiothiocarbonylthioazetidin-2-one

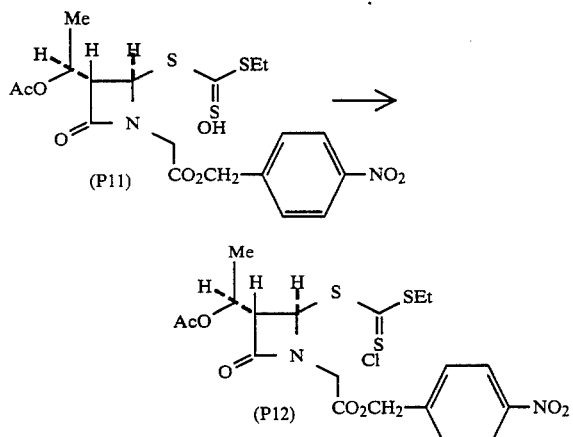

A solution of thionyl chloride (537 mg) in dry tetrahydrofuran (5 ml) was added dropwise over 10 minutes to a stirred mixture of the hydroxyester (P11) (1.51 g) and 2,6-lutidine (483 mg) in dry tetrahydrofuran (30 ml) at −10° C. The mixture was stirred at −10° C. for 10 minutes, filtered and evaporated. The residual gum was re-evaporated from dry toluene (2×3 ml) to give the chloroester (P12) (1.57 g) as a gum, $\nu_{max}$. (CHCl$_3$) 1790 and 1745 cm$^{-1}$.

PREPARATION 10

(3RS,4SR)-3-[1-(RS)-Acetoxyethyl]-4-ethylthiothiocarbonylthio-1-(1-p-nitrobenzyloxycarbonyl-1-triphenylphosphoranylidenemethyl)azetidin-2-one

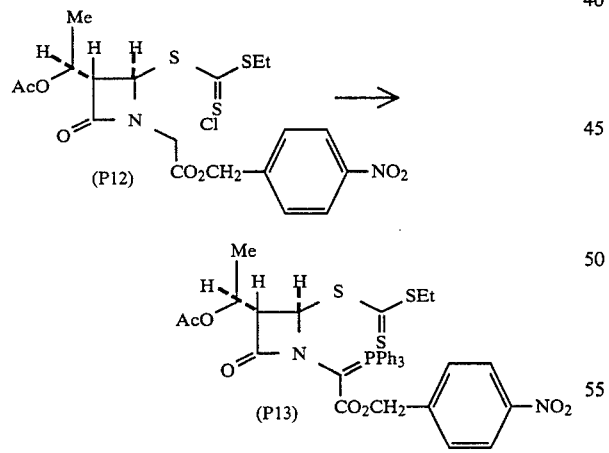

A mixture containing the chloroester (P12) (1.57 g), triphenylphosphine (1.58 g) and 2,6-lutidine (387 mg) in dry dioxan (30 ml) was stirred at 60° C. under dry argon for 24 hours. The mixture was cooled, filtered and the filtrate concentrated. The mixture was diluted with ethyl acetate (50 ml) and washed with N hydrochloric acid, brine, saturated sodium bicarbonate solution and brine. The dried (MgSO$_4$) organic layer was evaporated and the residue chromatographed on silica gel eluting with ethyl acetate/petroleum ether mixtures to give the phosphorane (P13) (1.12 g) as an amorphous solid, $\nu_{max}$. (CHCl$_3$) 1760, 1625 cm$^{-1}$.

PREPARATION 11

(5RS,6SR,8SR) and (5RS,6RS,8RS)-p-Nitrobenzyl 6-(1-Acetoxyethyl)-2-ethylthiophenem-3-carboxylate

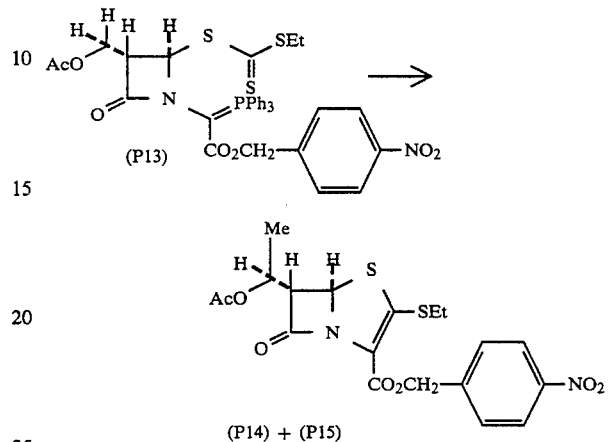

The phosphorane (P13) (1.04 g) was heated in refluxing xylene (1000 ml) under dry argon for 10 hours. The mixture was evaporated and chromatographed to give two products. The less polar product, the (5RS,6SR,8SR) penem ester (P14) (262 mg) was obtained as a solid, m.p. 143°–144° C. (needles ex ethyl acetate/petroleum ether); $\lambda_{max}$. (EtOH) 339 ($\epsilon_m$ 9,600) and 261 n.m. (14,400); $\nu_{max}$. (CHCl$_3$) 1785, 1740, 1695 cm$^{-1}$; δ ppm (CDCl$_3$) 1.37 (3H, t, J 7.4 Hz), 1.44 (3H, d, J 6.4 Hz), 2.09 (3H, s), 2.84–3.13 (2H, m), 3.96 (1H, dd, J 1.6 and 4.0 Hz), 5.1–5.5 (3H, m), 5.54 (1H, d, J 1.6 Hz), 7.62 (2H, d, J 8.6 Hz), 8.22 (2H, d, J 8.6 Hz). (Found: C, 50.5; H, 4.4; N, 6.2; S, 14.0; M+, 452.0721. C$_{19}$H$_{20}$N$_2$O$_7$S$_2$ requires C, 50.5; H, 4.4; N, 6.2; S, 14.2%; M, 452.0712). The more polar product, the (5RS,6RS,8RS) penem ester (P15) (15 mg) was also obtained as a solid, m.p. 179°–181° C. (needles ex ethyl acetate/petroleum ether); $\lambda_{max}$. (EtOH) 336 ($\epsilon_m$ 10,300) and 261 n.m. (15,500); $\nu_{max}$. (CHCl$_3$) 1795, 1735, 1690 cm$^{-1}$; δ ppm (CDCl$_3$) 1.21–1.39 (6H, m), 2.09 (3H, s), 2.87–3.14 (2H, m), 4.04 (1H, dd, J 4.1 and 7.8 Hz), 5.09–5.55 (3H, m), 5.73 (1H, d, J 4.1 Hz), 7.61 (2H, d, J 8.7 Hz), 8.22 (2H, d, J 8.7 Hz). (Found: M+, 452.0692. C$_{19}$H$_{20}$N$_2$O$_7$S$_2$ requires 452.0712).

PREPARATION 12 p-Nitrobenzyl 3-Mercaptopropionate

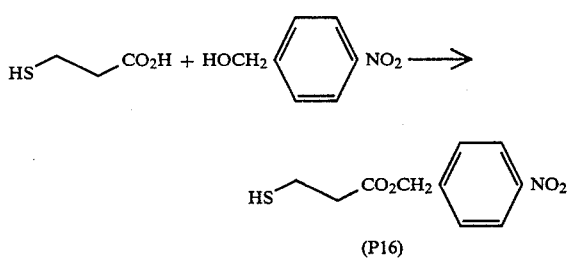

A mixture of 3-mercaptopropionic acid (5.3 mg), p-nitrobenzyl alcohol (7.65 g) and p-toluenesulphonic acid monohydrate (0.2 g) was heated in refluxing benzene (50 ml) for 8 hours with provision for azeotropic removal of water. The mixture was cooled and washed with saturated sodium bicarbonate solution (20 ml) and brine (3×10 ml). The dried (MgSO$_4$) organic layer was evaporated and chromatographed to give the ester (P16) (7.8 g) as an oil, $\nu$max (Film) 2580 w, 2460 w, 1740 cm$^{-1}$; δ ppm (CDCl$_3$) 1.45–1.85 (1H, m, exch. D$_2$O), 2.75–2.95 (4H, m, collapses to s on exch. D$_2$O), 5.30 (2H, s) 7.59 (2H, d, J 9 Hz), 8.28 (2H, d, J 9 Hz).

PREPARATION 13

L-(N-p-Nitrobenzyloxycarbonyl)cysteine Ethyl Ester

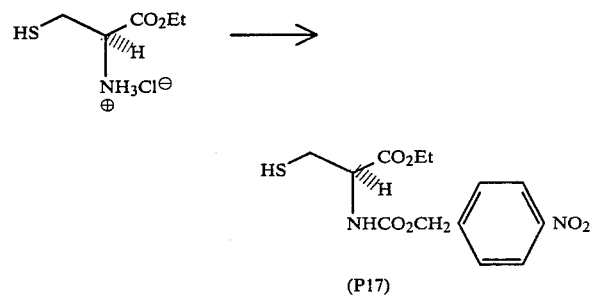

(P17)

Di-isopropylethylamine (3.99 ml) was added to a stirred, ice bath cooled, suspension of L-cysteine ethyl ester hydrochloride (1.86 g) in acetonitrile (10 ml) under dry argon. After 5 minutes the stirred, ice bath mixture was treated, in one portion, with chlorotrimethylsilane (1.64 ml). The mixture was stirred for a further 10 minutes and treated, dropwise over 5 minutes, with a solution of p-nitrobenzylchloroformate (2.16 g) in acetonitrile (5 ml). After the addition was complete the mixture was treated with di-isopropylethylamine (1.73 ml). The mixture was stirred for 30 minutes at ice bath temperature and then for a further 30 minutes whilst it attained room temperature. The mixture was poured into ice water (25 ml) and extracted with methylene chloride (2×25 ml). The combined extracts were washed with water (5 ml), N. hydrochloric acid (2 ml), saturated sodium bicarbonate solution (5 ml), and brine (5 ml). The dried (MgSO$_4$) organic layer was evaporated and chromatographed to give the N-protected cysteine ester (P17) (1.56 g) as a solid, $\nu$max (CHCl$_3$) 3420, 1730 cm$^{-1}$; δ ppm (CDCl$_3$) 1.27 (3H, t, J 7 Hz) partially obscuring 1.45 (1H, d, J 9 Hz, each D$_2$O), 3.00 (2H, dd, J 5 and 9 Hz, collapses to d, J 5 Hz on each D$_2$O), 4.26 (2H, q, J 7 Hz), 4.63 (1H, dt, J 5 and 8 Hz, collapses to t, J 5 Hz on each D$_2$O), 5.25 (2H, s), 5.90 br (1H, d, J 8 Hz, each D$_2$O), 7.57 (2H, d, J 9 Hz), 8.27 (2H, d, J 9 Hz).

EXAMPLE 1 p-Nitrobenzyl 6,6-dimethyl-2-ethylsulphinylpenem-3-carboxylate (2)

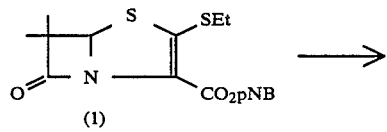

(1)

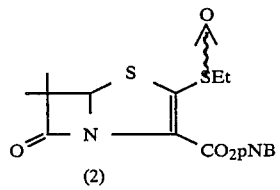

(2)

A solution of the penem (1) (370 mg, 0.94 mmol) in dry dichloromethane (25 ml) at 0° under argon was treated with m-chloroperbenzoic acid (259 mg, 1.50 mmol). After ten minutes the reaction mixture was washed with dilute sodium bicarbonate solution and brine then dried and evaporated. Chromatography on silica gel (230–400 mesh) eluting with ethyl acetate/petroleum mixtures afforded the sulphoxides (2). The less polar product, the sulphoxide (2) Isomer A (160 mg, 42%) was obtained as a light yellow solid, m.p. 120°–2° (plates from ethyl acetate/petroleum) $\lambda_{max}$. (EtOH) 347 n.m. ($\epsilon_m$ 5,000), 261 (9, 300); $\nu_{max}$. (CHCl$_3$) 1795, 1705, 1610 cm$^{-1}$; δ 1.40 (3H, t, J 8 Hz), 1.54 (3H, s), 1.56 (3H, s), 3.10 (2H, q, J 8 Hz), 5.22 and 5.47 (2H, centres of ABq, J 14 Hz), 5.68 (1H, s), 7.59 (2H, d, J 9 Hz), 8.23 (2H, d, J 9 Hz). (Found: M+ 410.0613. C$_{17}$H$_{18}$N$_2$O$_6$S$_2$ requires M 410.0603).

The more polar product, the sulphoxide (2) Isomer B (80 mg, 21%), was obtained as a gum, $\nu_{max}$. (CHCl$_3$) 1795, 1700, 1610 cm$^{-1}$. δ(CDCl$_3$) 1.42 (3H, t, J 8 Hz), 1.56 (6H, s), 3.08 (2H, q, J 8 Hz), 5.22 and 5.48 (2H, centres of ABq, J 14 Hz), 5.53 (1H, s), 7.63 (2H, d, J 9 Hz), 8.23 (2H, d, J 9 Hz). (Found: M+ 410.0615. C$_{17}$H$_{18}$N$_2$O$_6$S$_2$ requires M 410.0603).

The 6,6-dimethylpenem starting material (1) was itself synthesised according to the following reaction sequence:

Me$_2$C=CHOCOMe + ClSO$_2$NCO $\longrightarrow$

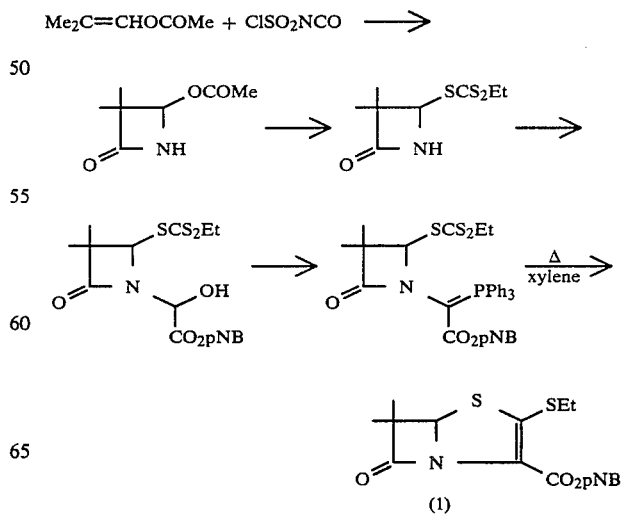

(1)

EXAMPLE 2 p-Nitrobenzyl 6,6-dimethyl-2-ethylthiopenem-3-carboxylate (1)

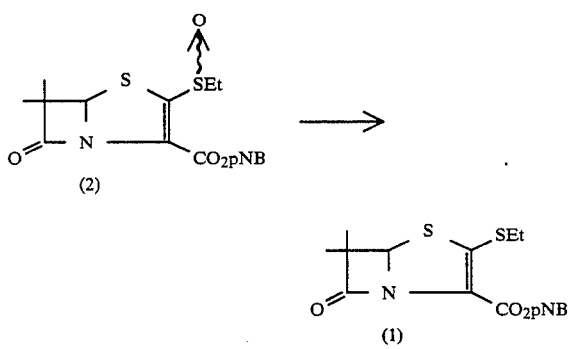

A solution of the sulphoxide (2), isomer A, (30 mg, 0.073 mmol) in dry DMF (10 mls) at −40° under argon was treated with a solution of sodium thioethoxide (6.6 mg, 0.079 mmol) in DMF (0.1 ml). After forty minutes the reaction mixture was poured into ethyl acetate (50 ml) and washed well with dilute hydrochloric acid solution (4×20 ml) and brine (10 ml). The dried organic phase was evaporated and chromatographed on silica gel eluting with ethyl acetate/petroleum mixtures to give the penem (1) (10 mg, 35%). This material was identical (t.l.c. and i.r.) with that previously obtained.

EXAMPLE 3 p-Nitrobenzyl 6,6-dimethyl-2-phenylthiopenem-3-carboxylate (3)

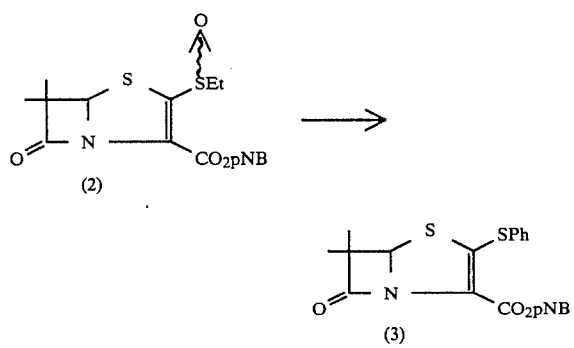

A solution of the sulphoxide (2), Isomer A, (65 mg, 0.159 mmol) in dry DMF (20 ml) under argon at −50° was treated with a solution of triethylamine (18.75 mg, 0.186 mmol) in DMF (0.1 ml) and a solution of thiophenol (20.46 mg, 0.186 mmol) in DMF (0.1 ml). After ten minutes the reaction mixture was poured into ethyl acetate (100 ml) and washed well with dilute hydrochloric acid (5×50 ml) and brine (40 ml). The dried organic phase was evaporated and chromatographed on silica gel eluting with ethyl acetate/petroleum mixtures to give the penem (3) (58 mg, 83%) m.p. 153°–4° (needles from ethyl acetate/petroleum); $\lambda_{max}$. (EtOH) 337 n.m. ($\epsilon_m$ 12,680), 262 (17,340); $\nu_{max}$. (CHCl$_3$) 1785, 1695 cm$^{-1}$; $\delta$ (CDCl$_3$) 1.39 (3H, s), 1.49 (3H, s), 5.23 and 5.55 (2H, centres of ABq, J 13 Hz), 5.32 (1H, s), 7.25–7.75 (7H, m) 8.23 (2H, d, J 8 Hz). (Found: C, 57.2; H, 4.1; N, 6.5; S, 14.4. $C_{21}H_{18}N_2O_5S_2$ requires C, 57.0; H, 4.1; N, 6.3; S, 14.5%).

EXAMPLE 4 p-Nitrobenzyl 6,6-dimethyl-2-phenylthiopenem-3-carboxylate (3)

A solution of the sulphoxide (2), Isomer B, (80 mg, 0.195 mmol) in dry DMF (25 ml) under argon at −50° C. was treated with a solution of triethylamine (23.0 mg, 0.228 mmol) in DMF (0.1 ml) and thiophenol (25.1 mg, 0.228 mmol) in DMF (0.1 ml). After twenty minutes the reaction mixture was poured into ethyl acetate (120 ml) and washed well with dilute hydrochloric acid solution (5×60 ml) and brine (50 ml). The dried organic phase was chromatographed on silica gel eluting with ethyl acetate/petroleum mixtures to give the penem (3) (40 mg, 46%) identical with previously obtained material.

EXAMPLE 5 p-Nitrobenzyl 6,6-dimethyl-2-(2-pyridylthio)penem-3-carboxylate (4)

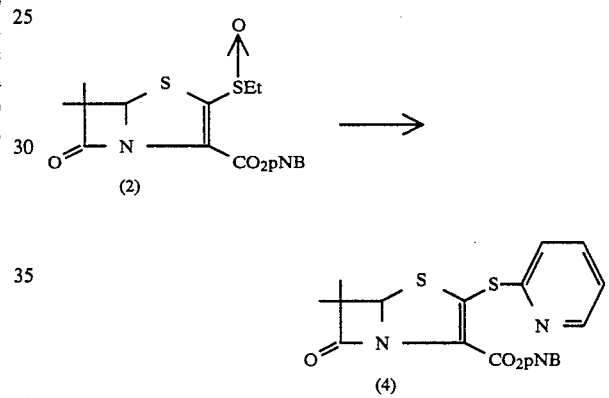

A solution of the sulphoxide (2), Isomer A, (45 mg, 0.11 mmol) in DMF (10 ml) at −35° under argon was treated with a solution of the sodium salt of 2-mercaptopyridine (16 mg, 0.12 mmol) in DMF (0.5 ml). After forty minutes the reaction mixture was poured into ethyl acetate (50 ml) and washed well with dilute hydrochloric acid (4×20 ml) and brine (10 ml). The dried organic phase was evaporated and chromatographed on silica gel eluting with ethyl acetate/petroleum mixtures to give the penem (4) (8 mg, 15%) as a gum. $\nu_{max}$. (CHCl$_3$) 1785, 1700 cm$^{-1}$; $\delta$ (CDCl$_3$) 1.45 (3H, s), 1.52 (3H, s), 5.22 and 5.51 (2H, centres of ABq, J 14 Hz), 5.38 (1H, s), 7.20–7.38 (2H, m), 7.55–7.76 (3H, m), 8.20 (2H, d, J 8 Hz), 8.52–8.70 (1H, m).

EXAMPLE 6 p-Nitrobenzyl 2-ethylsulphinylpenem-3-carboxylate (6)

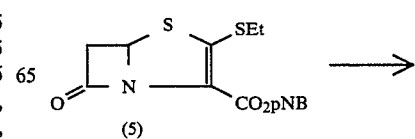

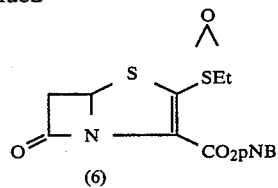

(6)

A solution of m-chlorperbenzoic acid (670 mg) in chloroform (5 ml) was added dropwise in five minutes to a stirred, ice-bath-cooled, solution of the penem ester (5) (1.09 g) in chloroform (20 ml). After a further fifteen minutes at ice-bath temperature the mixture was allowed to attain room temperature (fifteen minutes) and was washed with sodium bicarbonate solution and brine. The dried (MgSO$_4$) organic layer was evaporated and the residue chromatographed on silica gel eluting with ethyl acetate/petroleum ether mixtures to give two fractions. The less polar fraction, Isomer A of the sulphoxide (6) (373 mg), was obtained as clusters of tiny rods, m.p. 132°–134° C. (ethyl acetate/petroleum ether), $\lambda_{max.}$ (EtOH) 261 ($\epsilon_m$ 13,250) and 347 n.m. (7,145); $\nu_{max.}$ (CHCl$_3$) 1800, 1705 cm$^{-1}$; δ ppm (CDCl$_3$) 1.41 (3H, t, J 7 Hz), 3.11 (2H, q, J 7 Hz), 3.63 (1H, dd, J 2 and 17 Hz), 3.92 (1H, dd, J 4 and 17 Hz), 5.21 and 5.44 (2H, ABq, J 14 Hz), 5.89 (1H, dd, J 2 and 4 Hz), 7.58 (2H, d, J 9 Hz), 8.24 (2H, d, J 9 Hz). (Found: C, 47.2; H, 3.7; N, 7.3; S, 16.8. C$_{15}$H$_{14}$N$_2$O$_6$S$_2$ requires C, 47.1; H, 3.7; N, 7.3; S, 16.8%). The more polar fraction, Isomer B of the sulphoxide (6) (234 mg), was obtained as needles, m.p. 128°–130° C. (ethyl acetate/petroleum ether); $\lambda_{max.}$ (EtOH) 260 ($\epsilon_m$ 12,675) and 345 n.m. (7,700); $\nu_{max.}$ (CHCl$_3$) 1800, 1700 cm$^{-1}$; δ ppm (CDCl$_3$) 1.41 (3H, t, J 7 Hz), 3.07 (2H, q, J 7 Hz), 3.67 (1H, dd, J 2 and 16 Hz), 3.94 (1H, dd, J 4 and 16 Hz), 5.22 and 5.44 (2H, ABq, J 13 Hz), 5.76 (1H, dd, J 2 and 4 Hz), 7.60 (2H, d, J 8½ Hz), 8.23 (2H, d, J 8½ Hz). (Found: C, 47.2; H, 3.7; N, 7.3; S, 16.7. C$_{15}$N$_{14}$N$_2$O$_6$S$_2$ requires C, 47.1; H, 3.7; N, 7.3; S, 16.8%).

EXAMPLE 7 p-Nitrobenzyl 2-phenylthiopenem-3-carboxylate (7)

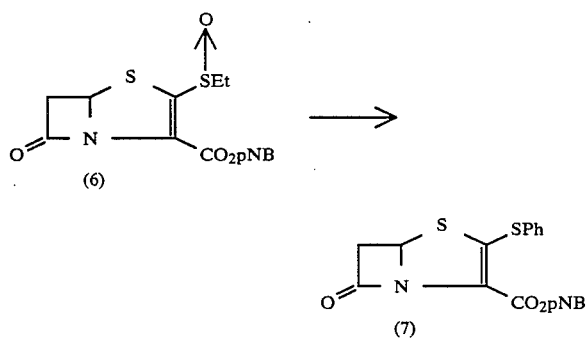

A solution of the sulphoxide (6), Isomer A, (57 mg, 0.15 mmol) in dry DMF (20 ml) under argon at −50° was treated with a solution of triethylamine (14.15 mg, 0.176 mmol) in DMF (0.1 ml) and a solution of thiophenol (19.36 mg, 0.176 mmol) in DMF (0.1 mls). After thirty minutes the reaction mixture was poured into ethyl acetate (100 ml) and washed well with dilute hydrochloric acid (5×50 ml) and brine (40 ml). The dried organic phase was evaporated and chromatographed on silica gel eluting with ethyl acetate/petroleum mixtures to give the penem (7) (25 mg, 40%), m.p. 152°–4° (needles from ethyl acetate/petroleum) $\nu_{max.}$ (CHCl$_3$) 1790, 1680 cm$^{-1}$; δ (CDCl$_3$) 3.35 (1H, dd, J 2, 16 Hz), 3.74 (1H, dd, J 4, 16 Hz), 5.26 and 5.50 (2H, centres of ABq, J 13 Hz), 5.54 (1H, dd, J 2, 4 Hz), 7.18–7.80 (7H, m), 8.23 (2H, d, J 9 Hz). (Found: M+ 414.0365: C$_{19}$H$_{14}$N$_2$O$_5$S$_2$ requires M 414.0344).

EXAMPLE 8 p-Nitrobenzyl 2-phenylthiopenem-3-carboxylate (7)

A solution of the sulphoxide (6), Isomer B, (42 mg, 0.11 mmol) in dry DMF (20 ml) was sequentially treated with a solution of thiophenol (14.3 mg, 0.13 mmol) in DMF (0.1 ml) and a solution of triethylamine (13.1 mg, 0.13 mmol) in DMF (0.1 ml). After thirty minutes the reaction mixture was poured into ethyl acetate (100 ml) and washed well with dilute hydrochloric acid solution (4×50 ml) and brine (40 ml). The dried organic phase was evaporated and chromatographed on silica eluting with ethyl acetate/petroleum mixtures to give the penem (7) (8 mg, 18%) identical with previously obtained material.

EXAMPLE 9 p-Nitrobenzyl (2(2-pyridylthio)penem-3-carboxylate (8)

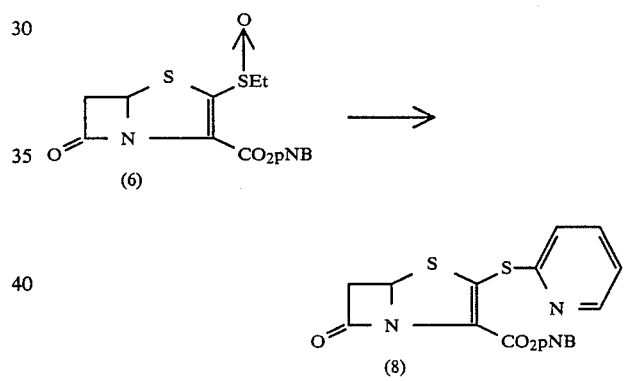

(a) The penem sulphoxide (6), Isomer B, (50 mg) was dissolved in a mixture of methylene choride (5 ml) and water (2 ml), cooled in an ice-bath and treated with the sodium salt of 2-mercaptopyridine (26 mg) followed by cetyltriethylammonium chloride (two drops of a 50% aqueous solution). The mixture was stirred at ice-bath temperature for forty minutes and diluted with methylene chloride (10 ml). The organic layer was separated and washed with brine (3×2 ml). The dried (MgSO$_4$) organic layer was evaporated and the residue chromatographed on silica gel eluting with ethyl acetate/petroleum ether mixtures to give the desired penem ester (8) (19 mg) m.p. 133°–4° (plates ex ethyl acetate/petroleum ether), $\lambda_{max.}$ (EtOH) 261 ($\epsilon_m$ 16,720) and 338 n.m. (11,650); $\nu_{max.}$ (CHCl$_3$) 1795, 1690 cm$^{-1}$; δ ppm (CDCl$_3$) 3.47 (1H, dd, J 1.9 and 16.0 Hz), 3.81 (1H, dd, J 3.6 and 16.0 Hz), 5.25 and 5.48 (2H, ABq, J 13 Hz), 5.59 (1H, dd, J 1.9 and 3.6 Hz), 7.2–8.0 (5H, m), 8.21 (2H, d, J 8 Hz), 8.5–8.7 (1H, m). (Found: M+, 415.0332. C$_{18}$H$_{13}$N$_3$O$_5$S$_2$ requires M, 415.0368).

(b) The above experiment was repeated using penem sulphoxide (6), Isomer A, to give the penem ester (8) in 14% yield.

EXAMPLE 10 p-Nitrobenzyl 2-(2-pyridylthio)penem-3-carboxylate (8)

A solution of the sulphoxide (6), Isomer A, (10 mg, 0.025 mmol), triethylamine (10 mg, 0.010 mmol) and 2-mercaptopyridine (11 mg, 0.010 mmol) in dry THF (2 ml) was stirred at room temperature for sixteen hours. The reaction mixture was poured into ethyl acetate and washed with dilute hydrochloric acid solution and brine. The dried organic phase was evaporated and chromatographed on silica gel eluting with ethyl acetate/petroleum mixtures to give the penem (8) (2 mg). This material was identical (t.l.c. and i.r.) with that previously obtained.

EXAMPLE 11 p-Nitrobenzyl 2-(2-pyridylthio)penem-3-carboxylate (8)

A solution of the sulphoxide (6), Isomer B, (10 mg, 0.025 mmol) triethylamine (10 mg, 0.010 mmol) and 2-mercaptopyridine (11 mg, 0.010 mmol) in dry THF (2 ml) was stirred at room temperature for one hour. The reaction mixture was poured into ethyl acetate and washed with dilute hydrochloric acid and then brine. The dried organic phase was chromatographed on silica gel eluting with ethyl acetate/petroleum mixtures to give the penem (8) (2 mg). This material was identical (t.l.c. and i.r.) with that previously obtained.

EXAMPLE 12

Sodium 2-(2-pyridylthio)penem-3-carboxylate (9)

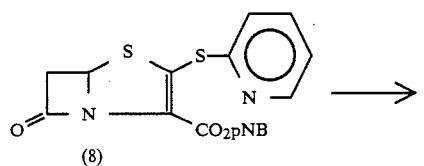

The penem ester (8) (35 mg) was dissolved in a mixture of dioxane (4 ml) and water (1 ml) and hydrogenated over 5% palladium on charcoal (52 mg) for one hour. A further amount of catalyst (35 mg) was added and the hydrogenation was continued for a further thirty minutes. A 1% solution of sodium bicarbonate (0.71 ml) was added and the mixture filtered through Kieselguhr. The mixture was then evaporated to low volume and chromatographed on Biogel P2 200–400 mesh, eluting with water. The appropriate fractions were combined and evaporated to afford the sodium salt (9) as an amorphous solid (15 mg), $\lambda_{max}$. (H$_2$O) 316 n.m. ($\epsilon_m$ 5590), 240 (5540); $\nu_{max}$. (KBr) 1770, 1600 cm$^{-1}$.

The MIC of this compound required to inhibit the growth of various bacteria are tabulated below:

EXAMPLE 13 p-Nitrobenzyl 2-[2-(Z)-Ethoxycarbonylvinylthio]penem-3-carboxylate (10)

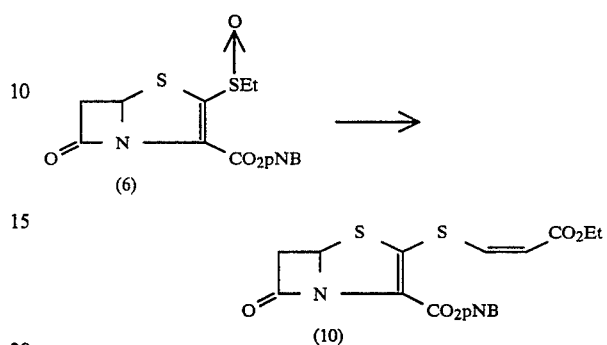

An ice-bath cooled solution of (Z)-2-carboethoxyvinylisothiuonium chloride (27 mg) in water (1 ml) was treated with 1N sodium hydroxide solution (0.26 ml). After 2 minutes at ice-bath temperature the stirred mixture was treated with a solution of the penem sulphoxide (6), Isomer B, (50 mg) in methylene chloride (3 ml) followed by cetyltriethylammonium chloride (one drop of a 50% aqueous solution). The mixture was stirred at ice-bath temperature for 20 minutes and worked up as in Example 9 to give the penem ester (10) (9 mg) as a solid, m.p. 175°–177° C. (ethylacetate/petroleum ether); $\lambda_{max}$. (EtOH) 267 ($\epsilon_m$ 14,065) and 342 n.m. (12,515); $\nu_{max}$. (CHCl$_3$) 1800, 1700 cm$^{-1}$; δ ppm (CDCl$_3$) 1.30 (3H, t, J 7 Hz), 3.55 (1H, dd, J 16 and 2.0 Hz), 3.88 (1H, dd, J 16 and 3.8 Hz), 4.24 (2H, q, J 7 Hz), 5.25 and 5.48 (2H, ABq, J 14 Hz), 5.71 (1H, dd, J 3.8 and 2.0 Hz), 6.01 (1H, d, J 10.1 Hz), 7.31 (1H, d, J 10.1 Hz), 7.64 (2H, d, J 8½ Hz), 8.22 (2H, d, J 8½ Hz). (Found: M+, 436.0418. C$_{18}$H$_{16}$N$_2$O$_7$S$_2$ requires M, 436.0397).

EXAMPLE 14

Sodium 2-[2-(Z)-Ethoxycarbonylvinylthio]penem-3-carboxylate (11)

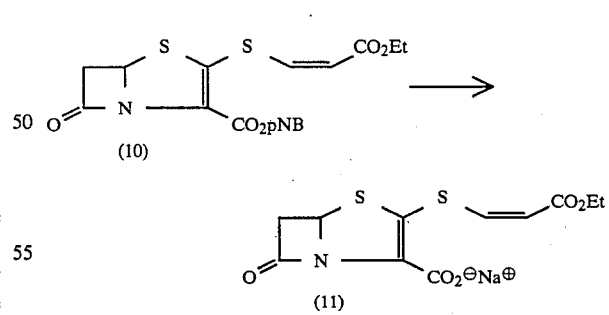

The penem ester (10) (20 mg) was dissolved in a mixture of dioxan (8 ml) and water (2 ml) and hydrogenated over 5% palladium/charcoal catalyst (30 mg) at S.T.P. for 30 minutes. Fresh catalyst (20 mg) was added and the hydrogenation continued for a further 30 minutes. A 1% solution of sodium bicarbonate (0.38 ml) was added and the mixture was worked up as for Example 12 to give the sodium salt (11) (8 mg) as an amorphous solid, $\lambda_{max}$. (H$_2$O) 273 ($\epsilon_m$ 7415) and 326 n.m. (9600); $\nu_{max}$. (KBr) 3700–3000, 1775, 1695, 1600, 1570 cm$^{-1}$; δ ppm (D₂O) 1.12 (3H, t, J 7 Hz), 3.41 (1H, d, J 17 Hz with further fine coupling), 3.67 (1H, dd, J 17 and 3½ Hz), 4.05 (2H, q, J 7 Hz), 5.60 (1H, d, J 3½ Hz with further fine coupling ≯1 Hz), 5.86 (1H, d, J 10 Hz), 7.44 (1H, d, J 10 Hz).

EXAMPLE 15 p-Nitrobenzyl 2-[2-(Z)-Acetamidovinylthio]penem-3-carboxylate (12)

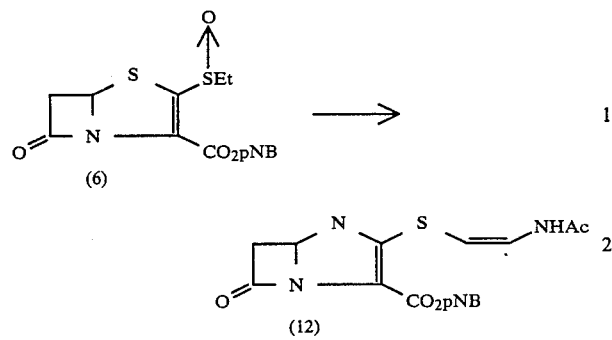

The penem sulphoxide (6), Isomer B, (38 mg) was dissolved in a mixture of methylene chloride (4 ml) and water (2 ml), cooled in an ice-bath, and treated with sodium 2-(Z)-acetamidovinylmercaptide (1.3 equivalents) followed by cetyltriethylammonium chloride (two drops of a 50% aqueous solution). The mixture was stirred at ice-bath temperature for 20 minutes and worked up as for Example 9 to give the penem ester (12) (20 mg) as a solid, m.p. 188°–190° C. (fine needles ex ethyl acetate/petroleum ether); $\lambda_{max.}$ (EtOH) 254 ($\epsilon_m$ 22,380) and 341 (12,760); $\nu_{max.}$ (Nujol) 3350, 1805, 1690 cm⁻¹; δ ppm (CDCl₃) 2.15 (3H, s), 3.53 (1H, dd, J 1.7 and 16.5 Hz), 3.84 (1H, dd, J 3.9 and 16.5 Hz), 5.26 and 5.53 (2H, ABq, J 13.8 Hz), 5.49 (1H, d, J 8.3 Hz), 5.70 (1H, dd, J 1.7 and 3.9 Hz), 7.45 (1H, dd, J 8.3 and 11.6 Hz), 7.63 (2H, d, J 8.6 Hz), 7.83 (1H, d, J 11.6 Hz), 8.24 (2H, d, J 8.6 Hz). (Found: C, 48.6; H, 3.5; N, 10.0; S, 15.2; M⁺, 421.0410. C₁₇H₁₅N₃O₆S₂ requires C, 48.5; H, 3.6; N, 10.0; S, 15.2%; M, 421.0402).

EXAMPLE 16

Sodium 2-{2-(Z)-Acetamidovinylthio}penem-3-carboxylate (13)

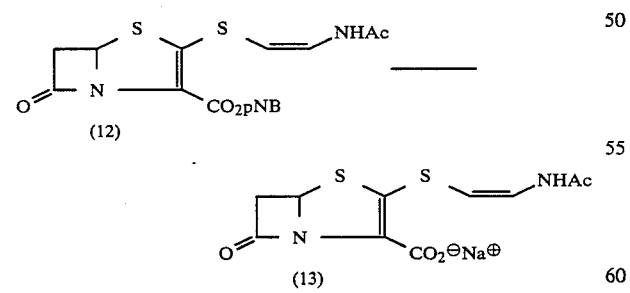

The penem ester (12) (26 mg) was dissolved in a mixture of dioxan (8 ml) and water (2 ml) and hydrogenated over 5% palladium/charcoal catalyst (39 mg) at S.T.P. for 30 minutes. Fresh catalyst (26 mg) was added and the hydrogenation continued for a further 30 minutes. A 1% sodium bicarbonate solution (0.52 ml) was added and the mixture was worked up as for Example 12 to give the sodium salt (13) (8 mg) as a buff coloured amorphous solid, $\lambda_{max.}$ (H₂O) 243 ($\epsilon_m$ 12,740) and 321 n.m. (7, 380); $\nu_{max.}$ (KBr) 3700–2700, 1765, 1680, 1620 and 1590 sh. cm⁻¹; ppm (D₂O) 1.93 (3H, s), 3.28 (1H, dd, J 1.6 and 17 Hz), 3.59 (1H, dd, J 4 and 17 Hz), 5.51 (d, J 8 Hz) overlaying 5.45–5.50 (m) together 2H, 7.01 (1H, d, J 8 Hz).

EXAMPLE 17 p-Nitrobenzyl 2-{2-pyrimidylthio}penem-3-carboxylate (14)

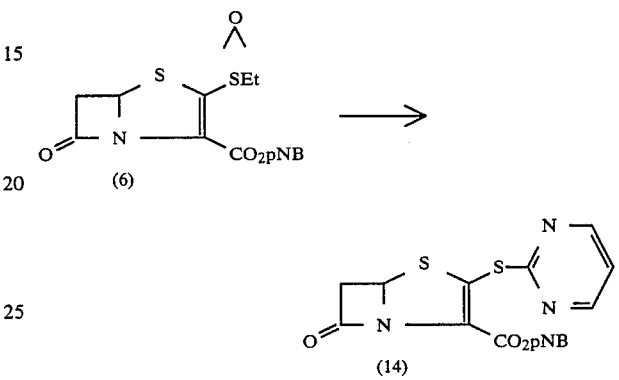

The penem sulphoxide (6), Isomer B, (60 mg) was dissolved in a mixture of methylene chloride (5 ml) and water (2 ml), cooled in an ice-bath and treated with sodium 2-mercaptopyrimidine (32 mg) followed by cetyltriethylammonium chloride (two drops of a 50% aqueous solution). The mixture as stirred at ice-bath temperature for one hour and treated with sodium-mercaptopyrimidine (10 mg). After a further 20 minutes at ice-bath temperature the mixture was worked up as for Example 9 to give the penem ester (14) (16 mg) as a solid, $\lambda_{max.}$ (EtOH) 264 ($\epsilon_m$ 15,620) and 344 n.m. (9,240); $\nu_{max.}$ (CHCl₃) 1795, 1705 br. cm⁻¹; δppm (CDCl₃) 3.55 (1H, dd, J 2 and 16 Hz), 3.87 (1H, dd, J 4 and 16 Hz), 5.22 and 5.45 (2H, ABq, J 14 Hz), 5.67 (1H, dd, J 2 and 4 Hz), 7.11 (1H, t, J 5 Hz), 7.59 (2H, d, J 8 Hz), 8.20 (2H, d, J 8 Hz), 8.59 (2H, d, J 5 Hz). (Found: M⁺, m/e 416; {M-C₂H₂O}⁺, 374.0177. C₁₇H₁₂N₄S₂O₅ requires M, 416, M-C₂H₂O, 374.0142).

EXAMPLE 18

Sodium 2-{2-pyrimidylthio}penem-3-carboxylate (15)

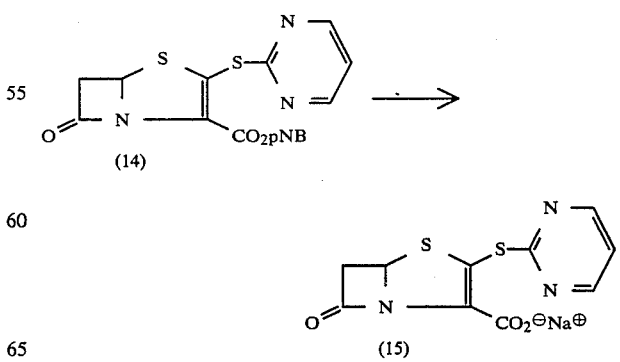

The penem ester (14) (20 mg) was dissolved in a mixture of dioxan (8 ml) and water (2 ml) and hydrogenated over 5% palladium/charcoal catalyst (30 mg) at S.T.P. for 30 minutes. Fresh catalyst (20 mg) was added and the hydrogenation continued for a further 30 minutes. A 1% sodium bicarbonate solution (0.40 ml) was added and the mixture was worked up as for Example 12 to give the sodium salt (15) (6 mg) as an amorphous solid, $\lambda_{max}$. (H$_2$O) 240 ($\epsilon_m$ 5,520) and 316 n.m. (3, 100).

EXAMPLE 19 p-Nitrobenzyl 2-(2-Aminophenylthio)penem-3-carboxylate (16)

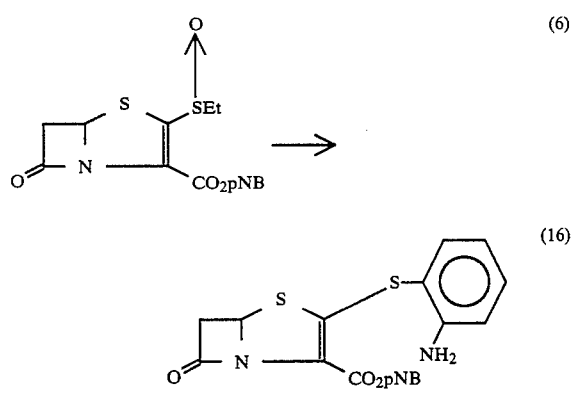

(a) A solution of the penem sulphoxide (6) Isomer B, (60 mg, 0.158 mmol) in dry THF (3 ml) was sequentially treated with 2-aminothiophenol (30 mg, 0.237 mmol) and triethylamine (24 g, 0.237 mmol). After five minutes the reaction mixture was poured into ethyl acetate and washed with dilute hydrochloric acid solution, dilute sodium bicarbonate solution and brine. The dried organic phase was evaporated and the residue chromatographed on silica eluting with ethyl acetate/petroleum ether mixtures to give the penem ester (16) (51 mg, 76%) as a light yellow solid, $\nu_{max}$. (CHCl$_3$) 3490, 3390, 1795, 1730, 1690 cm$^{-1}$; δ (CDCl$_3$) 3.35 (1H, dd, J 2 17 Hz), 3.70 (1H, dd, J 4, 17 Hz), 4.38 (2H, bs., exch.), 0.5.21 and 5.47 (2H, ABq, J 14 Hz), 5.51 (1H, dd, J 2, 4 Hz), 6.72 (1H, d, J 8 Hz), 7.2–7.45 (3H, m), 7.62 (2H, d, J 8 Hz), 8.19 (2H, d, J 8 Hz). (Found: M+, 429.0443. C$_{19}$H$_{15}$N$_3$O$_5$S$_2$ requires M, 429.0450).

(b) The above experiment was repeated using penem sulphoxide (6), Isomer A, to give the penem ester (16) in 62% yield. Note: Omission of triethylamine in the above experiments resulted in an increase in reaction time.

EXAMPLE 20

2-(2-Aminophenylthio)penem-3-carboxylic acid (17)

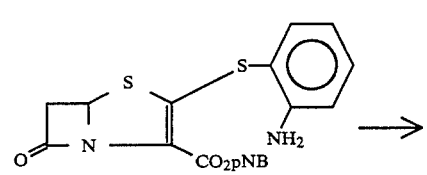

-continued

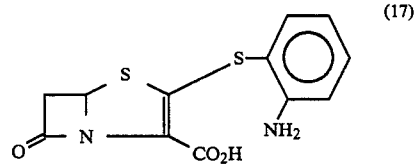

A solution of the penem ester (16) (55 mg) in dioxane (1 ml), ethanol (2.5 ml), ethyl acetate (5 ml) and water (2.5 ml) was hydrogenated over 10% palladium on charcoal catalyst for 45 minutes. The reaction mixture was filtered through Kieselguhr, washing the pad well with water and ethyl acetate. The reaction mixture was evaporated to low volume and chromatographed on Biogel P2 eluting with water. The appropriate fractions were combined and evaporated to give acid (17) (6 mg) as an amorphous solid, $\lambda_{max}$. (H$_2$O) 318 n.m., $\nu_{max}$. (KBr) 1765, 1600 cm$^{-1}$.

EXAMPLE 21

Sodium 2-Ethylsulphinylpenem-3-carboxylate (19)

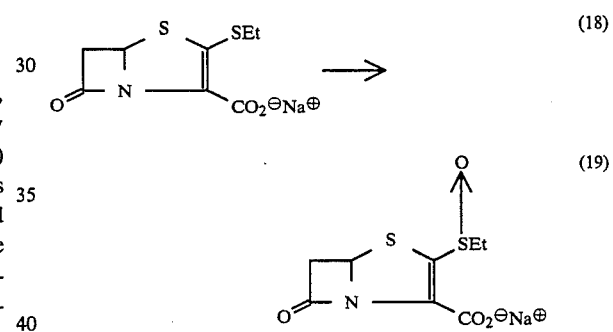

A solution of 2-ethylthiopenem sodium salt (18) (15 mg) in water (1 ml) at 5° was treated with m-chloroperbenzoic acid (10 mg) and the mixture stirred vigorously. After 30 minutes the reaction mixture was filtered and the filtrate chromatographed on Biogel P2 eluting with water. The appropriate fractions were combined and evaporated to give the sulphoxide sodium salt (19) (7 mg) as an amorphous solid, $\lambda_{max}$. (H$_2$O) 325 n.m.

EXAMPLE 22

(5RS,6SR,8SR)-p-Nitrobenzyl 6-(1-Acetoxyethyl)-2-ethylsulphinylpenem-3-carboxylate

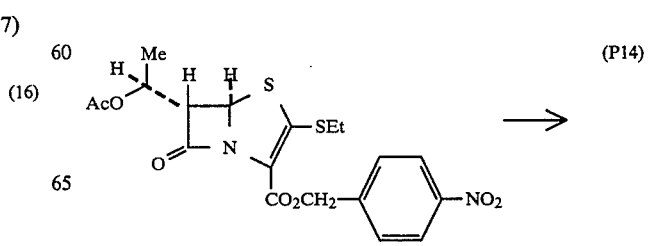

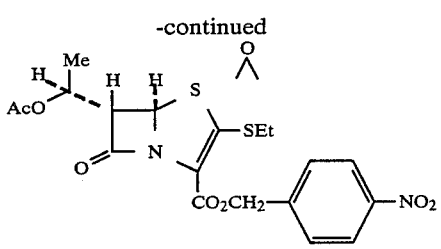
(20)

A solution of m-chloroperbenzoic acid (45 mg) in methylene chloride (1 ml) was added, in one portion, to a vigorously stirred, ice-bath cooled, mixture of the penem ester (P14) (90 mg), methylene chloride (5 ml) and saturated sodium bicarbonate solution (5 ml). The mixture was stirred at ice-bath temperature for 10 minutes and diluted with methylene chloride (10 ml). The organic layer was separated and washed with brine (3×2 ml), dried (MgSO$_4$), evaporated and chromatographed to give the sulphoxide (20) (53 mg), an approximately 1:1 mixture of isomers, as an amorphous solid, $\nu_{max}$. (CHCl$_3$) 1805, 1740 and 1710 cm$^{-1}$; δ ppm (CDCl$_3$) 1.32–1.50 (6H, m), 2.10 (3H, s), 2.9–3.3 (2H, m), 4.11 (1H, dd, J 2 and 4 Hz), 5.23 and 5.46 (ABq, J 14 Hz) plus 5.1–5.5 (m) together 3H, 5.59 (½H, d, J 2 Hz), 5.70 (½H, d, J 2 Hz), 7.59 and 7.60 (2H, each d, J 8 Hz), 8.25 (2H, d, J 8 Hz).

EXAMPLE 23

(5RS,6SR,8SR)-p-Nitrobenzyl 6-(1-Acetoxyethyl)-2-(2-pyridylthio)penem-3-carboxylate

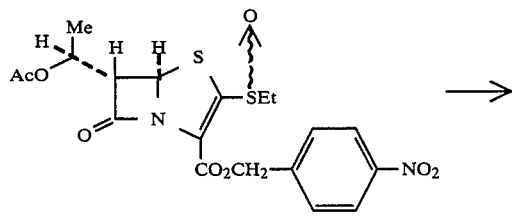
(20)

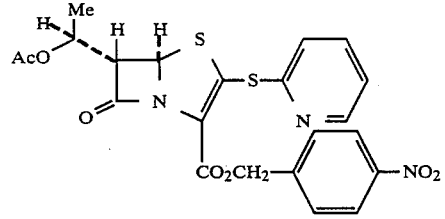
(21)

A stirred, ice-bath cooled, mixture of the penem sulphoxide (20) (50 mg), methylene chloride (5 ml), and water (2 ml) was treated with sodium 2-mercaptopyridine (16 mg) followed by benzylidimethyl-n-hexadecylammonium chloride (47 mg) portionwise over 5 minutes. The cooled mixture was stirred for a further 5 minutes, diluted with methylene chloride (10 ml) and washed successively with 5% citric acid (2 ml), brine (2 ml), saturated sodium bicarbonate solution (2 ml) and brine (3×2 ml). The dried (MgSO$_4$) organic layer was evaporated and chromatographed to give the penem ester (21) (22 mg) as a solid, m.p. 140°–142° C. (needles ex ethyl acetate/petroleum ether); $\lambda_{max}$. (EtOH) 262 ($\epsilon_m$ 17,790) and 339 n.m. (12,090); $\nu_{max}$. (CHCl$_3$) 1790, 1735, 1700 cm$^{-1}$; δ ppm (CDCl$_3$) 1.43 (3H, d, J 7 Hz), 2.10 (3H, s), 3.96 (1H, dd, J 1.7 and 3.9 Hz), 5.22–5.32 (1H, m), 5.30 and 5.50 (2H, ABq, J 14 Hz), 5.44 (1H, d, J 1.7 Hz), 7.25–734 (1H, m), 7.54–7.74 (4H, m), 8.20–8.27 (2H, m), 8.58–8.62 (1H, m). (Found: C, 52.8; H, 4.0; N, 8.2; S, 12.5. C$_{22}$H$_{19}$N$_3$O$_7$S$_2$ requires C, 52.7; H, 3.8; N, 8.4; S, 12.8%).

EXAMPLE 24

(5RS)-p-Nitrobenzyl 6-Ethylidene-2-(2-p-nitrobenzyloxycarbonylaminoethylthio)penem-3-carboxylate

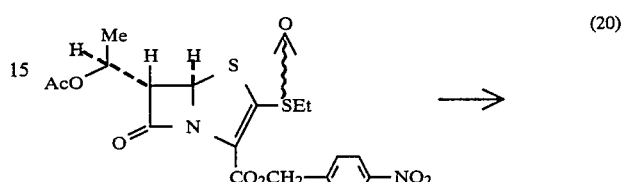
(20)

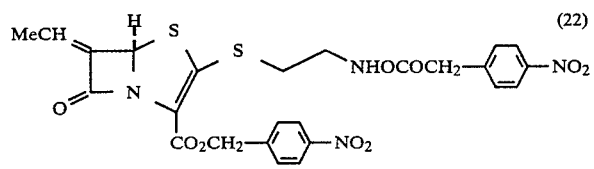
(22)

2-p-Nitrobenzyloxycarbonylaminoethanethiol (49 mg) was dissolved in 0.1N sodium hydroxide solution (1.9 ml), cooled in an ice-bath, and treated with a solution of the sulphoxide (20) (79 mg) in methylene chloride (5 ml). The stirred, ice-bath cooled, mixture was treated, portionwise over 5 minutes, with benzyldimethyl-n-hexadecylammonium chloride (75 mg). The cooled mixture was stirred for a further 10 minutes, diluted with methylene chloride (10 ml), and washed with 5% citric acid (2 ml), brine (2 ml), saturated sodium bicarbonate (2 ml), and brine (3×2 ml). The dried (MgSO$_4$) organic layer was evaporated and chromatographed to give the 6-ethylidenepenem ester (22) (46 mg), an approximately 2:1 mixture of E and Z isomers, as an amorphous solid, $\lambda_{max}$. (EtOH) 262 ($\epsilon_m$ 23,600) and approximately 314 n.m. (inflection); $\nu_{max}$. (CHCl$_3$) 3450, 1785, 1730, 1705 slight shoulder cm$^{-1}$; δ ppm (CDCl$_3$) 1.81 (⅓ CH$_3$, d, J 7 Hz), 2.10 (⅔ CH$_3$, d, J 7 Hz), 2.95–3.20 (2H, m), 3.35–3.65 (2H, m), 5.18 (s) plus 5.19 and 5.49 (ABq), J 14 Hz) plus 5.1–5.5 (m) together 5H, 6.02 (⅔H, q, J 7 Hz), 6.13 and 6.18 (1H, each s), 6.47 (⅓H, q, J 7 Hz), 7.48 and 7.62 (4H, each d, J 8 Hz), 8.19 (4H, d, J 8 Hz).

EXAMPLE 25

(5RS)-p-Nitrobenzyl 6-Ethylidene-2-ethylsulphinylpenem-3-carboxylate

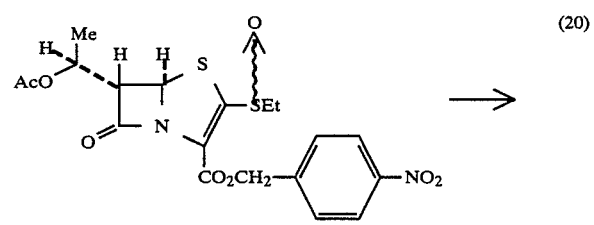
(20)

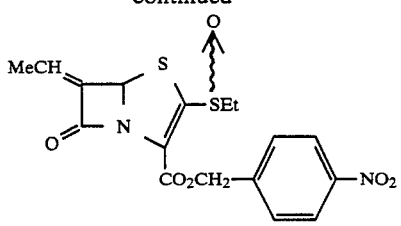

A solution of the penem sulphoxide (20) (60 mg) in dry methylene chloride (3 ml) was cooled to −20° C. and treated, dropwise, over 3 minutes, with a solution of 1,8-diazabicyclo[5.4.0]undec-7-ene (27 mg) in dry methylene chloride (4.2 ml). The mixture was stirred at −20° C. for 10 minutes and worked up as for Example 24 to give, after chromatography, the 6-alkylidenepenem sulphoxide ester (23) (30 mg) as an amorphous solid $\lambda_{max}$. (EtOH) 213 ($\epsilon_m$ 22,380), 261 (13,570) and 356 n.m. (5,420); $\nu_{max}$. (CHCl$_3$) 1790 and 1705 cm$^{-1}$; δ ppm (CDCl$_3$) 1.35–1.50 (3H, m), 1.87 and 1.89 (½ CH$_3$, each d, J 7 Hz), 2.16 and 2.18 (½ CH$_3$, each d, J 7 Hz), 3.03–3.24 (2H, m), 5.21–5.32 (1H, m), 5.41–5.52 (1H, m), 6.12 and 6.17 (½H, each dq, J 7 and 0.8 Hz), 6.23 and 6.25 (½H, each broadened s), 6.38 (½H, broadened s), 6.57 and 6.61 (½H, each dq, J 7 and 1.2 Hz), 7.60–7.68 (2H, m), 8.23–8.29 (2H, m). (Found: M$^+$, 408.0410. C$_{17}$H$_{16}$N$_2$O$_6$S$_2$ requires M, 408.0447).

EXAMPLE 26

(5RS)-p-Nitrobenzyl 6-Ethylidene-2-(2-p-nitrobenzyloxycarbonylaminoethylthio)penem-3-carboxylate

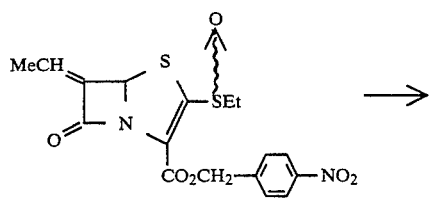

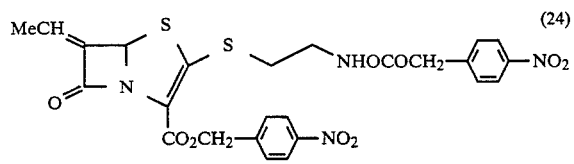

2-p-Nitrobenzyloxycarbonylaminoethanethiol (5.6 mg) was dissolved in 0.1N sodium hydroxide solution (0.22 ml), cooled in an ice-bath, and treated with a solution of the penem sulphoxide (9 mg) in methylene chloride (1 ml). The stirred, ice-bath cooled, mixture was treated, portionwise over 1 minute, with benzyldimethyl-n-hexadecylammonium chloride (8.7 mg). The mixture was stirred at ice-bath temperature for 10 minutes and worked up as for Example 24 to give the 6-ethylidenepenem ester (24) (5 mg), an approximately 1:1 mixture of E and Z isomers, as a gum (infra-red and n.m.r. data consistent with those obtained in Example 24.

EXAMPLE 27

(5RS)-p-Nitrobenzyl 6-Ethylidene-2-(2-hydroxyethylthio)penem-3-carboxylate

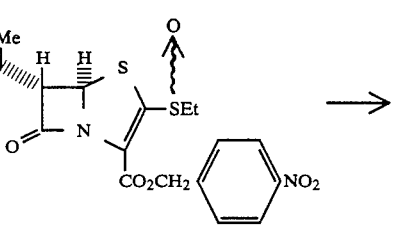

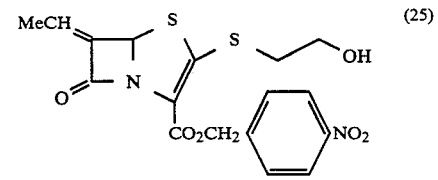

A 0.1N solution of sodium hydroxide (1.8 ml) was added dropwise over 3 minutes to a stirred, ice bath cooled, solution of the penem sulphoxide (20) (70 mg), 2-mercaptoethanol (14 mg), and benzyldimethyl-n-hexadecylammonium chloride (71 mg) in methylene chloride (5 ml). After stirring at ice bath temperature for a further 10 minutes the mixture was worked up as for Example 24 to give the 6-ethylidenepenem ester (25) (21 mg), an approximately 1:1 mixture of E and Z-isomers, as a solid, $\lambda$max (EtOH) 260 (Em 15380) and 322 nm (8550); $\nu$max (CHCl$_3$) 3600–3200, 1780, 1690 cm$^{-1}$; δppm (CDCl$_3$) 1.86 (1½H, d, J 7 Hz), 1.93 (1H, t, J 6 Hz), 2.14 (1½H, d, J 7 Hz), 3.04–3.26 (2H, m), 3.84–3.92 (2H, m), 5.24 and 5.50 (ABq, J 14 Hz) plus 5.25 and 5.49 (ABq, J 14 Hz) together 2H, 6.04 (½H, q, J 7 Hz), 6.16 (½H, s), 6.19 (½H, s), 6.50 (½H, q, J 7 Hz), 7.64–7.67 (2H, m), 8.20–8.26 (2H, m). (Found: M$^+$, 408.0442. C$_{17}$H$_{16}$N$_2$O$_6$S$_2$ requires M, 408.0447).

EXAMPLE 28

(5RS)-Sodium 6-Ethylidene-2-(2-hydroxyethylthio)penem-3-carboxylate

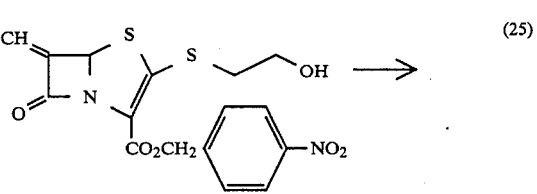

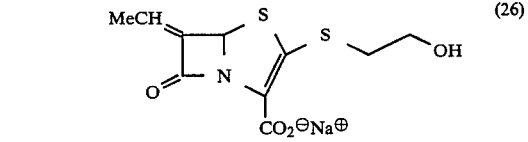

The penem ester (25, a 1:1 mixture of E and Z isomers) (28 mg) was dissolved in a mixture of dioxan (8 ml) and water (2 ml) and was hydrogenated over 5% palladium/charcoal catalyst (42 mg) at S.T.P. for 40 minutes. Fresh catalyst (28 mg) was added and the hydrogenation was continued for a further 40 minutes.

A 1% sodium bicarbonate solution (0.58 ml) was added and the mixture was worked up as for Example 12 to give the sodium salt (26) (11.4 mg) as an amorphous solid, λmax (H$_2$O) 300 (Em 3710) and approximately 335 nm (inflection).

EXAMPLE 29

(5RS)-p-Nitrobenzyl 6-Ethylidene-2-(2-p-nitrobenzyloxycarbonylethylthio)-penem-3-carboxylate

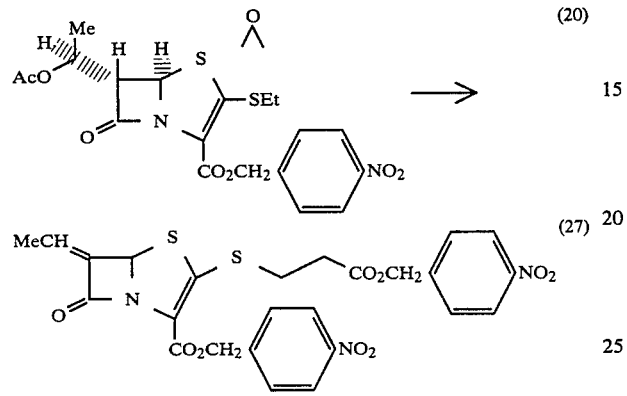

A 0.1N solution of sodium hydroxide (1.2 ml) was added dropwise over 3 minutes to a stirred, ice bath cooled, solution of the penem sulphoxide (20) (47 mg), p-nitrobenzyl 3-mercaptopropionate (P16) (29 mg) and benzyldimethyl-n-hexadecylammonium chloride (48 mg) in methylene chloride (5 ml). After stirring at ice bath temperature for 15 minutes the mixture was worked up as for Example 24 to give the 6-ethylidenepenem ester (27) (32 mg), an approximately 3:2 mixture of Z and E isomers, as a pale yellow solid, λmax (EtOH) 260 (Em 21,410) and 314 nm (7000); νmax (CHCl$_3$) 1785, 1740, 1695 cm$^{-1}$; δppm (CDCl$_3$) 1.83 (1.2H, d, J 7 Hz), 2.11 (1.8H, d, J 7 Hz), 2.7–3.0 (2H, m), 3.0–3.3 (2H, m), 5.18 and 5.48 (ABq, J 14 Hz) plus 5.21 (s) together 4H, 6.00 (0.6H, q, J 7 Hz), 6.14 and 6.17 (1H, each s), 6.46 (0.4H, q, J 7 Hz), 7.48 and 7.61 (4H, each d, J 9 Hz), 8.19 (4H, d, J 9 Hz).

EXAMPLE 30

(5RS)-2-(2-Carboxyethylthio)-6-ethylidenepenem-3-carboxylic Acid Disodium Salt

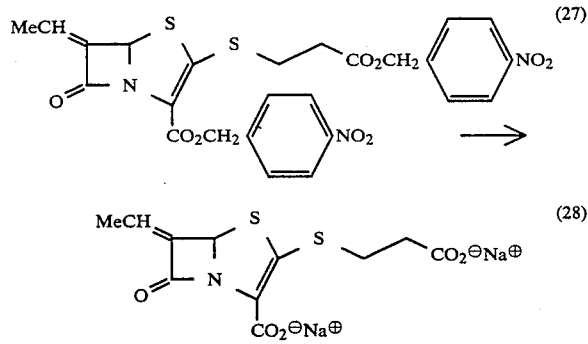

The penem ester (27, a 3:2 mixture of Z and E isomers) (30 mg) was dissolved in a mixture of dioxan (8 ml) and water (2 ml) and was hydrogenated over 5% palladium/charcoal catalyst (45 mg) at S.T.P. for 40 minutes. Fresh catalyst (30 mg) was added and the hydrogenation was continued for a further 40 minutes. A 1% solution of sodium bicarbonate (0.88 ml) was added and the mixture was worked up as for Example 12 to give the disodium salt (28) (10.1 mg), a 3:2 mixture of Z and E isomers, as an amorphous solid, λmax (H$_2$O) 304 nm (Em 2515); δppm (D$_2$O) 1.84 (1.2H, d, J 7 Hz), 2.04 (1.8H, d, J 7 Jz), 2.50–2.67 (2H, m) 2.95–3.25 (2H, m), 6.19 (q, J 7 Hz) and 6.21 (s) together 1.2H, 6.29 (0.4H, s), 6.53 (0.4H, q, J 7 Hz).

EXAMPLE 31

(5RS,2'R)-p-Nitrobenzyl 2-(2-Ethoxycarbonyl-2-p-nitrobenzyloxycarbonylaminoethylthio)-6-ethylidenepenem-3-carboxylate

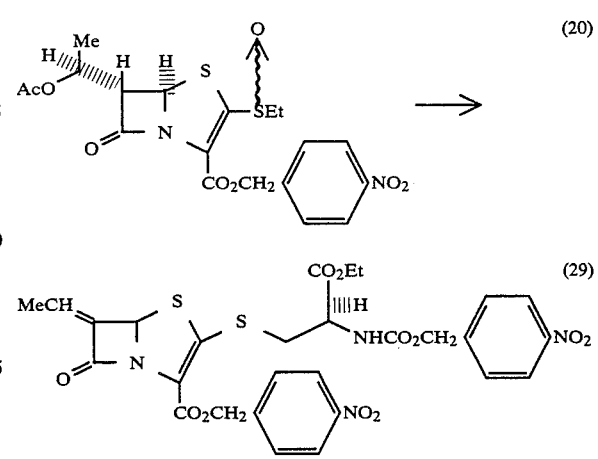

A 0.1N solution of sodium hydroxide (1.2 ml) was added dropwise over 3 minutes to a stirred, ice bath cooled, solution of the penem sulphoxide (20) (47 mg), L-(N-p-nitrobenzyloxycarbonyl) cysteine ethyl ester (P17) (39 mg), and benzyldimethyl-n-hexadecylammonium chloride (48 mg) in methylene chloride (5 ml). The mixture was stirred at ice bath temperature for a further 15 minutes and worked up as for Example 24 to give the 6-ethylidenepenem ester (29) (20 mg), a 2:1 mixture of Z and E isomers, as an amorphous solid, λmax (EtOH) 262 (Em 24,460) and approximately 315 nm (inflection); νmax (CHCl$_3$) 3420, 1785, 1730 cm$^{-1}$; δppm (CDCl$_3$) 1.25–1.35 (3H, m), 1.82 and 1.84 (1H, each d, J 7 Hz), 2.12 and 2.13 (2H, each d, J 7 Hz), 3.1–3.7 (2H, m), 4.2–4.3 (2H, m), 4.6–4.8 (1H, m), 5.2–5.3 (3H, m), 5.46–5.54 (1H, m), 5.69 br (1H, d, J 7 Hz, collapses to a broad s on irradiation at 4.68 ppm), 6.02 br (⅔H, q, J 7 Hz), 6.09 br (⅓H, s, collapses to d, J 1 Hz on irradiation at 2.13 ppm), 6.14 (⅓H, broad s, collapses to d J 1 Hz on irradiation at 2.13 ppm), 6.15 and 6.17 (⅓H, each broad s, collapsing to 2 d, J 1 Hz on irradiation at 1.83 ppm), 6.47 and 6.48 (⅓H, each d q, J 7H and 1 Hz), 7.51 (2H, d, J 9 Hz), 7.65 (2H, d, J 9 Hz), 8.22 (4H, d, J 9 Hz).

EXAMPLE 32

(5RS,2'R)-2-(2-Amino-2-ethoxycarbonylethylthio)-6-ethylidenepenem-3-carboxylic Acid

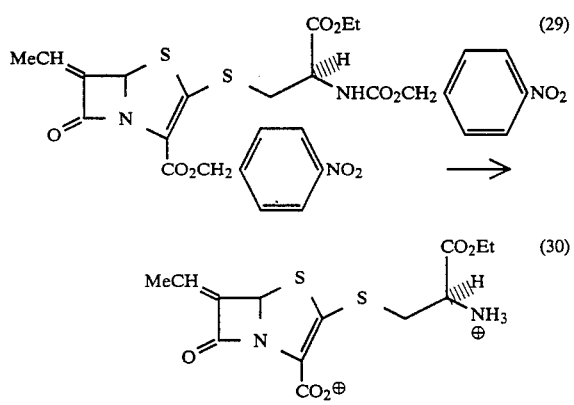

The penem ester (29, a 2:1 mixture of Z and E isomers) (20 mg) was dissolved in a mixture of ethyl acetate (5 ml), ethanol (2.5 ml) and water (2.5 ml) and was hydrogenated over 5% palladium/charcoal catalyst (30 mg) at S.T.P. for 40 minutes. Fresh catalyst (20 mg) was added and the hydrogenation was continued for a further 40 minutes. The mixture was filtered through Kieselguhr, the residue being washed with ethyl acetate (5 ml) and water (2×3 ml). The aqueous layer was separated and washed with ethyl acetate (2 ml). The aqueous layer was evaporated and the residue chromatographed on Biogel P2 eluting with water. The appropriate fractions were evaporated and the residue re-evaporated from ethanol (1 ml) and dry toluene (2×1 ml) to give, after trituration with dry ether, the amino acid (30) (2.5 mg), a 3:2 mixture of Z and E isomers, as an amorphous solid, δppm (D$_2$O) (inter alia) 1.84 (1.2H, d, J 7 Hz), 2.05 (1.8H, d, J 7 Hz).

EXAMPLE 33

(5RS,6SR,8SR)-p-Nitrobenzyl-6-(1-Acetoxy-1-phenyl-methyl)-2-ethylsulphinylpenem-3-carboxylate

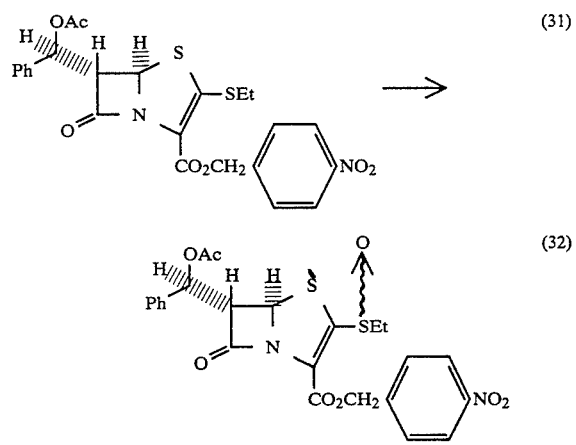

A solution of m-chloroperbenzoic acid (131 mg) in methylene chloride (3 ml) was added, in one portion, to a vigorously stirred, ice bath cooled, mixture of the penem ester (31, our co-pending patent, U.K. Application No. 8013563) (300 mg), methylene chloride (15 ml) and saturated sodium bicarbonate solution (15 ml). After stirring at ice bath temperature for 15 minutes the mixture was diluted with methylene chloride (10 ml). The organic layer was separated and washed with brine (3×2 ml). The dried (MgSO$_4$) organic layer was evaporated and chromatographed to give the sulphoxide (32) (203 mg), a 1:1 mixture of isomers, as an amorphous solid, λmax (EtOH) 262 (Em 13,850) and 346 nm (6875); νmax (CHCl$_3$) 1800, 1740, 1705 cm$^{-1}$; δppm (CDCl$_3$) 1.39 (3H, t, J 7 Hz), 2.11 (3H, s), 2.82–3.22 (2H, m), 4.32–4.45 (1H, m), 5.21–5.41 (2H, ABq, J 14 Hz), 5.69 (½H, d, J 2 Hz), 5.82 (½H, d, J 2 Hz), 6.17 (1H, d, J 6 Hz), 7.35 (5H, m), 7.55 and 7.57 (2H, each d, J 9 Hz), 8.21 (2H, d, J 9 Hz).

EXAMPLE 34

(5RS)-p-Nitrobenzyl 2-(3-Acetamidoethylthio)-6-(Z)-benzylidenepenem-3-carboxylate

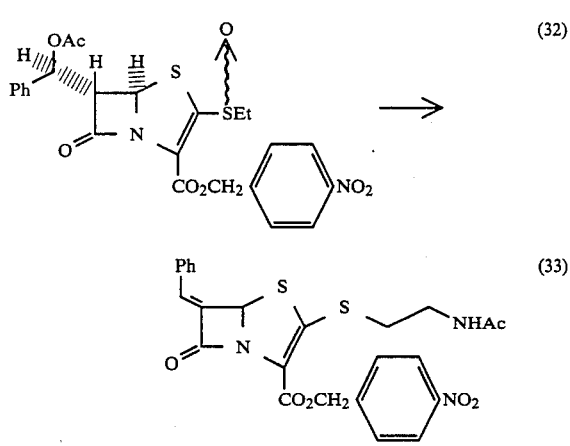

A 0.1N solution of sodium hydroxide (1.2 ml) was added dropwise over 3 minutes to a stirred, ice bath cooled, solution of the penem sulphoxide (32) (53 mg), 2-acetamidoethane thiol (14 mg) and benzyldimethyl-n-hexadecylammonium chloride (48 mg) in methylene chloride (5 ml). After stirring at ice bath temperature for a further 20 minutes the reaction was worked up as for Example 24 to give the 6-benzylidenepenem ester (33) (29 mg) as a yellow solid, λmax (EtOH) 287 (Em 27,820) and approximately 328 nm (inflection); νmax (Nujol) 3280, 1785, 1695, 1675 shoulder cm$^{-1}$; δppm [(CD$_3$)$_2$SO] 1.76 (3H, s), 2.9–3.2 (2H, m), 3.26–3.35 (m, partially obscured by H$_2$O peak), 5.34 and 5.47 (2H, ABq, J 13 Hz) 7.05 (1H, d, J<1 Hz), 7.39 (1H, d, J<1 Hz), 7.53 (5H, s), 7.74 (2H, d, J 8½ Hz), 8.15 (1H, t, J 6 Hz), 8.28 (2H, d, J 8½ Hz).

EXAMPLE 35

(5RS)-Sodium 2-(2-Acetamidoethylthio)-6-(Z)-benzylidenepenem-3-carboxylate

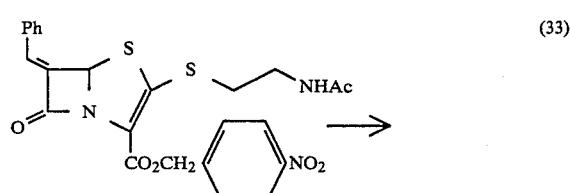

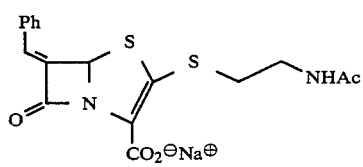

(34)

The penem ester (33) (26 mg) was dissolved in a mixture of dioxan (8 ml) and water (2 ml) and was hydrogenated over 5% palladium/charcoal catalyst (39 mg) at S.T.P. for 40 minutes. Fresh catalyst (26 mg) was added and the hydrogenation was continued for a further 40 minutes. A 1% solution of sodium bicarbonate (0.43 ml) was added and the mixture was worked up as for Example 12 to give the sodium salt (34) (7.6 mg) as an amorphous solid, λmax (H$_2$O) 291 (Em 16,630) and 370 nm (2240).

BIOLOGICAL DATA

Tables I and II show the antibacterial activity of several novel compounds of the present invention, in terms of their minimum inhibitory concentration (MIC).

TABLE I

| | In vitro antibacterial activity (μg/ml)* | | | | | |
|---|---|---|---|---|---|---|
| | Compound of Example No. | | | | | |
| Organism | (12) | (14) | (16) | (18) | (20) | (21) |
| *Citrobacter freundii* E8 | >100 | 31 | 25 | 100 | 500 | 125 |
| *Escherichia coli* O111 | 100 | 31 | 12.5 | 100 | 125 | 63.5 |
| *Klebsiella aerogenes* A | >100 | 31 | 25 | 100 | 125 | 250 |
| *Proteus mirabilis* 977 | >100 | 31 | 25 | 50 | 62 | 62.5 |
| *Salmonella typhimurium* CT10 | 100 | 16 | 12.5 | 50 | 62 | 125 |
| *Shigella sonnei* MB 11967 | >100 | 31 | 12.5 | 100 | 62 | 125 |
| *Bacillus subtilis* A | 10 | 2.0 | 3.1 | 12.5 | 8.0 | 31 |
| *Staphylococcus aureus* Oxford | 25 | 4.0 | 1.6 | 25 | 16 | 62.5 |
| *Staphylococcus aureus* Russell | 50 | 16 | 6.2 | 50 | 31 | 62.5 |
| *Streptococcus pneumoniae* CN 33 | 1.0 | — | 0.2 | 6.2 | ≦0.5 | 4.0 |
| *Streptococcus pyrogenes* CN 10 | 10 | 2.0 | 0.4 | 25 | ≦0.5 | 4.0 |

*Microtitre using Nutrient broth - inoculum 0.001 ml of a 10$^{-2}$ dilution for Gram-positive bacteria or a 10$^{-4}$ dilution for Gram-negative organisms.

TABLE II

| | In vitro antibacterial activity (μg/ml)* | | | |
|---|---|---|---|---|
| | Compound of Example No. | | | |
| Organism | (28) | (32) | (30) | (35) |
| *Citrobacter freundii* E8 | 100 | — | — | — |
| *Citrobacter freundii* Mantio | — | >100 | 62.5 | >500 |
| *Escherichia coli* O111 | >100 | 50 | 16 | >500 |
| *Escherichia coli* ESS | 100 | 12.5 | 4 | — |
| *Escherichia coli* JT 39 | >100 | 100 | 16 | >500 |
| *Proteus mirabilis* 977 | >100 | 25 | 125 | >500 |
| *Staphylococcus aureus* Oxford | 12.5 | 3.1 | 16 | 0.5 |
| *Staphylococcus aureus* Russell | 12.5 | 12.5 | 31.2 | 2 |
| *Streptococcus pneumoniae* CN 33 | 3.1 | — | — | — |

*Microtitre using nutrient broth - inoculum 0.001 ml of a 10$^{-2}$ dilution from Gram-positive bacteria or a 10$^{-4}$ dilution for Gram-negative organisms.

I claim:

1. A process for the preparation of a 2-thio penem derivative of formula (IV) or a pharmaceutically acceptable salt or in vivo hydrolysable ester thereof:

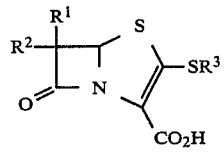

(IV)

wherein R$^1$ and R$^2$ are independently hydrogen; substituted or unsubstituted: C$_{1-10}$ alkyl, alkenyl and alkynyl having from 2–10 carbon atoms; cycloalkyl, cycloalkylalkyl, and alkylcycloalkyl, having 3–6 carbon atoms in the cycloalkyl ring and 1–6 carbon atoms in the alkyl moieties thereof; phenyl; aralkyl, aralkenyl, and aralkynyl wherein the aryl moiety is phenyl and the linear chain has 1–6 carbon atoms; wherein the substituent or substituents relative to the above named radicals are selected from the group consisting of: amino, alkanoylamino, mono- and di-alkylamino, hydroxyl, alkoxyl, alkanoyloxy, mercapto, alkylthio, phenylthio, sulfamoyl, amidino, guanidino, nitro, chloro, bromo, fluoro, cyano and carboxy, and wherein the alkyl moieties of the above-recited substituents have 1–6 carbon atoms; a free hydroxy or mercapto group; an amino or acylamino group of formula (d), (e), (f) or (g):

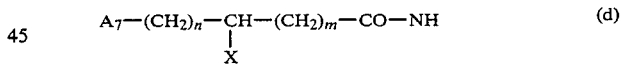

(d)

(e)

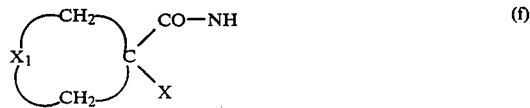

(f)

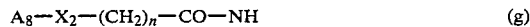

(g)

wherein n is 0, 1 or 2; m is 0, 1 or 2; A$_7$ is an alkyl group of 1–6 carbon atoms, a cycloalkyl group of 3–6 carbon atoms, cyclohexenyl, cyclohexadienyl, phenyl, hydroxyphenyl, thienyl or pyridyl group; x is a hydrogen, bromine or chlorine atom, a carboxylic acid, carboxylate ester, hydroxy, acetoxy, amino, ureido, guanidino or acetylureido group; A$_8$ is a phenyl, 2,5-dimethoxyphenyl, 2-alkoxy-1-naphthyl, isothiazolyl, 3-phenyl-5-methyl-4-isoxazolyl, 3-o-chlorophenyl-5-methyl-4-isoxazolyl, 3-o,o-dichlorophenyl-5-methyl-4-isoxazolyl, 3-o,o-fluorochlorophenyl-5-methyl-4-isoxazolyl, 3-phenyl-4-isoxazolyl, 3-o-chlorophenyl-4-isoxazolyl, 3-o,o-dichlorophenyl-4-isoxazolyl, 3-o,o-fluorochlorophenyl- 4-isoxazolyl group wherein the aryl moiety is phenyl unsubstituted or substituted by up to two halo atoms; $X_1$ is a $CH_2OCH_2$, $CH_2SCH_2$ or $(CH_2)_n$ group; and $X_2$ is an oxygen or sulphur atom; or together $R^1$ and $R^2$ represent a group $=CR^5R^6$ wherein $R^5$ and $R^6$ are the same or different and each represents hydrogen or a $C_{1-10}$ hydrocarbon group; and $R^3$ represents an organic radical having up to 18 carbon atoms selected from a saturated or unsaturated aliphatic, cycloaliphatic, cycloaliphaticaliphatic, phenyl or aralkyl, wherein the aryl moiety is phenyl and the alkyl part has 1-6 carbon atoms, or a heterocyclyl or heterocyclyl-alkyl radical having up to 10 carbon atoms and up to 4 ring hetero atoms selected from the group nitrogen, oxygen and/or sulphur, any of which $R^3$ groups may be optionally substituted by amino, mono-, di- and tri-($C_{1-6}$) alkylamino, $C_{1-6}$ alkanoylamino, hydroxyl, $C_{1-6}$ alkylthio, phenylthio, sulfamoyl, amidino, guanidino, nitro, chloro, bromo, fluoro, cyano, carboxyl, $C_{1-6}$ alkoxycarbonyl, and $C_{1-6}$ alkanoyloxy which process comprises reacting a sulphoxide of formula (V):

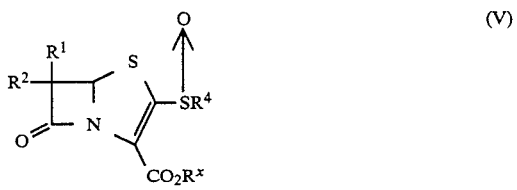

wherein $R^1$ and $R^2$ are as defined with respect to formula (IV) above, $R^x$ represents hydrogen or a salt, ester or anhydride of the carboxylic acid group which may be readily cleaved under conventional conditions, and $R^4$ is an organic radical as defined in relation to $R^3$ in formula (IV) provided that $R^4$ is different to $R^3$; with a thiol of formula (VI) or a reactive salt thereof:

$$R^3\!-\!SH \qquad (VI)$$

and thereafter if necessary carrying out one or more of the following steps:
 (i) removal of any carboxyl-blocking group $R^x$;
 (ii) converting the product to a pharmaceutically acceptable salt or in vivo hydrolysable ester group.

2. A process as claimed in claim 1 wherein $R^3$ is $C_{1-6}$ alkyl, $C_{2-6}$ alkenyl, aryl, aralkyl wherein the alkyl has 1∝6 carbon atoms, heterocyclyl or heterocyclylalkyl, wherein the alkyl has 1-3 carbon atoms, and the heterocyclyl ring comprises 4-6 atoms, up to 4 of which may be selected from oxygen and nitrogen; any group $R^3$ being optionally substituted.

3. A process as claimed in claim 2 wherein the optional substituent is amino, mono-, di-, and tri-($C_{1-6}$) alkylamino, $C_{1-6}$ alkanoylamino, hydroxyl, $C_{1-6}$ alkoxyl, mercapto, $C_{1-6}$ alkylthio, arylthio, sulfamoyl, amidino, guanidino, nitro, chloro, bromo, fluoro, cyano, carboxyl, $C_{1-6}$ alkoxycarbonyl and $C_{1-6}$ alkanoyloxy.

4. A process as claimed in claim 2 wherein $R^3$ is optionally substituted $C_{2-6}$ alkenyl, aryl or heterocyclyl.

5. A process as claimed in claim 1 wherein one of the groups $R^1$ and $R^2$ is hydrogen.

6. A process as claimed in claim 1 wherein one of the groups $R^1$ and $R^2$ is $C_{1-6}$ alkyl, optionally substituted with hydroxy or alkanoyloxy.

7. A process as claimed in claim 1 wherein $R^1$ and $R^2$ together represent a group $=CR^5R^6$ wherein $R^5$ and $R^6$ are independently hydrogen, $C_{1-6}$ alkyl or phenyl.

* * * * *